(12) United States Patent
Goulter et al.

(10) Patent No.: US 8,355,126 B2
(45) Date of Patent: Jan. 15, 2013

(54) HAND-HELD, SELF-CONTAINED OPTICAL EMISSION SPECTROSCOPY (OES) ANALYZER

(75) Inventors: John E. Goulter, Northridge, CA (US); Mark Hamilton, Upton, MA (US); Pratheev Sreetharan, Medford, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 125 days.

(21) Appl. No.: 12/036,039

(22) Filed: Feb. 22, 2008

(65) Prior Publication Data

US 2008/0212074 A1 Sep. 4, 2008

Related U.S. Application Data

(60) Provisional application No. 60/891,408, filed on Feb. 23, 2007.

(51) Int. Cl.
*G01J 3/30* (2006.01)
(52) U.S. Cl. .................. 356/318; 356/313
(58) Field of Classification Search .......... 356/317–318, 356/326–328, 313
See application file for complete search history.

(56) References Cited

U.S. PATENT DOCUMENTS

| | | | |
|---|---|---|---|
| 3,728,029 A * | 4/1973 | Hirschfeld | 356/308 |
| 4,641,968 A * | 2/1987 | Grandy | 356/313 |
| 4,734,776 A | 3/1988 | Wang et al. | |
| 4,986,658 A * | 1/1991 | Kim | 356/318 |
| 5,002,390 A * | 3/1991 | Gerlacher et al. | 356/328 |
| 5,319,437 A * | 6/1994 | Van Aken et al. | 356/328 |
| 5,426,305 A | 6/1995 | Siebentritt, Jr. et al. | |
| 5,444,520 A * | 8/1995 | Murano | 359/820 |
| 5,483,339 A * | 1/1996 | Van Aken et al. | 356/326 |
| 5,708,743 A | 1/1998 | DeAndrea et al. | |
| 5,712,841 A | 1/1998 | Opheij et al. | |
| 5,717,199 A | 2/1998 | Carbone et al. | |
| 5,719,672 A * | 2/1998 | Chien | 356/328 |
| 5,923,808 A | 7/1999 | Melling | |
| 6,031,233 A * | 2/2000 | Levin et al. | 356/326 |
| 6,501,547 B1 * | 12/2002 | Spencer et al. | 356/328 |
| 6,628,383 B1 | 9/2003 | Hilliard | |

(Continued)

FOREIGN PATENT DOCUMENTS

DE 199 00 308 A1 7/2000

(Continued)

OTHER PUBLICATIONS

EPO computer translation of DE 19900 308 A1, May 23, 2011, p. 1.*

(Continued)

*Primary Examiner* — Kara E Geisel
(74) *Attorney, Agent, or Firm* — Gordon Stewart

(57) ABSTRACT

A hand-held, self-contained, battery-powered test instrument for analyzing composition of a sample includes an exciter for exciting at least a portion of the sample, a compact cross-dispersed spectrometer for receiving an optical signal from the excited portion of the sample and a processor for processing spectral data about the optical signal from the spectrometer. The exciter may include a spark generator and a counter electrode, a laser or other device for generating the optical signal from the sample portion. The spectrometer has a wavelength range broad enough to enable the test instrument to detect and determine relative quantities of carbon, phosphorous, sulfur, manganese, silicon, iron and other elements necessary to identify common alloys. The spectrometer includes a structural member made of a light-weight material having a small coefficient of thermal expansion (CTE). The spectrometer is dimensionally stable over a range of expected ambient temperatures, without controlling the temperature of the spectrometer.

30 Claims, 18 Drawing Sheets

U.S. PATENT DOCUMENTS

| | | | |
|---|---|---|---|
| 6,801,595 | B2 | 10/2004 | Grodzins et al. |
| 7,304,741 | B2 * | 12/2007 | Sadeghi et al. ............... 356/417 |
| 7,336,989 | B2 | 2/2008 | Chuck et al. |
| 7,342,659 | B2 * | 3/2008 | Horn et al. ................... 356/328 |
| 2003/0071975 | A1 * | 4/2003 | Fujimori et al. ............... 353/31 |
| 2004/0096165 | A1 | 5/2004 | Childers et al. |
| 2004/0160602 | A1 * | 8/2004 | Eklin et al. .................... 356/313 |
| 2005/0030533 | A1 * | 2/2005 | Treado ........................... 356/318 |
| 2005/0229698 | A1 * | 10/2005 | Beecroft et al. ................ 73/300 |
| 2005/0248758 | A1 * | 11/2005 | Carron et al. .................. 356/301 |
| 2007/0229819 | A1 * | 10/2007 | Seaward et al. ............... 356/316 |
| 2008/0151241 | A1 * | 6/2008 | Lindfors et al. .............. 356/318 |
| 2008/0191137 | A1 * | 8/2008 | Poteet et al. .................. 250/372 |
| 2008/0198377 | A1 | 8/2008 | Joosten |

FOREIGN PATENT DOCUMENTS

| | | |
|---|---|---|
| JP | 06317471 | 11/1994 |
| JP | 11-183254 | 7/1999 |
| JP | 2002-226713 | 8/2002 |
| JP | 2004101226 | 4/2004 |
| JP | 2005-140565 A | 6/2005 |
| JP | 2006064449 | 3/2006 |
| WO | 2005096171 A2 | 10/2005 |

OTHER PUBLICATIONS

Bhaskaran et al., "SpectraCAM SPM-A Camera System with High Dynamic Range for Scientific and Medical Applications," SPIE Proceedings, pp. 1-9, (2005).

Fowler et al., "An Ultra Low Noise High Speed CMOS Linescan Sensor for Scientific and Industrial Applications," SPIE Proceedings, pp. 1-11, (2004).

Pain et al., "CMOS Image Sensors Capable of Time Delayed Integration," NASA Tech. Briefs, pp. 47-49, (2001).

True et al., "On the Implementation of Multielement Continuum Source Graphite Furnace Atomic Absorption Spectrometry Utilizing an Echelle/CID Detection System," Applied Spectroscopy, vol. 53 (No. 9), pp. 1102-1110, (1999).

Baird et al..,"Compact, Self-Contained Optical Spectrometer," Applied Spectroscopy, pp. 1699-1704, (1995).

Metorex, "ARC-MET 8000 Mobile Lab," product brochure, pp. 1-4, (2004).

J. Allington-Smith, "Spectroscopy Principles," Presentation, University of Durham, pp. 1-40.

Spectro, Spectro iSort—The New Arc for Metal Analysis; Simpler, Safer, Faster . . . , product brochure, http://www.spectro.cz/download/spectro_isort_brozura_en.pdf, pp. 1-4.

RTP Company, "End-Use Case Study—LCD Projector," http://www.rtpcompany.com/info/apps/stories/lcd/htm, pp. 1-2.

RTP Company, "Case Studies: PPS Applications," http://www.rtpcompany.com/info/apps/resin/pps/index.htm, p. 1.

TCR Engineering Services, "Positive Material Identification (PMI)," brochure, http://www.tcreng.com/services/positive-material-identification-pmi.shtml, pp. 1-2.

* cited by examiner

Optical emission spectrum obtained during evaporation of SO0N20B-250 Coating

ABOUT 1

HAND-HELD, SELF-CONTAINED OPTICAL EMISSION SPECTROSCOPY (OES) ANALYZER

The present application claims priority from U.S. Provisional Patent Application No. 60/891,408, titled "Hand-Held, Self-Contained Optical Emission Spectroscopy (OES) Analyzer," filed Feb. 23, 2007, which is incorporated in its entirety by reference herein.

The contents of commonly-assigned U.S. patent application Ser. No. 12/035,477, by Denis Baiko, et al., titled "Fast and Precise Time-Resolved Spectroscopy with Linear Sensor Array," filed Feb. 22, 2008, is incorporated in its entirety by reference herein.

The contents of commonly-assigned U.S. patent application Ser. No. (to be supplied), by John E. Goulter, et al., titled "A compact Cross-Dispersed Spectrometer for Extended Spectral Range," filed Feb. 22, 2008, is incorporated in its entirety by reference herein.

TECHNICAL FIELD

The present invention relates to optical emission spectroscopic (OES) analyzers and, more particularly, to self-contained, hand-held OES analyzers.

BACKGROUND ART

Analyzing chemical composition of samples is important in many contexts, including identifying and segregating metal types (particularly various types of iron and steel) in outdoor metal recycling facilities, quality control testing in factories and forensic work. Several analytical methods are available.

Optical emission spectroscopy (OES) is a mature, robust technology for the elemental analysis of materials. In OES, a small quantity of sample material is vaporized and excited above atomic ground state. Emissions characteristic of elements in the vaporized sample are captured by a light guide, which sends the light to a spectrometer, which produces and analyzes a spectrum from the light, so as to yield the elemental composition.

For metal samples, the prevalent techniques for generating an emission spectra use either an electric arc or a spark, or both, to vaporize a small quantity of the sample to be analyzed. Alternatively, laser-induced breakdown spectroscopy (LIBS) or glow discharge (GD) may be used to vaporize and excite an emission sample. A survey of OES analytical techniques may be found in Slickers, Automatic Atomic-Emission Spectroscopy, Second Edition (1993), which is incorporated by reference as if fully set forth herein.

In order to be confident that the composition deduced from a measurement, which typically tests a miniscule portion of the sample, is representative of the composition of the entire sample, minimizing effects from, for example, inclusions, matrixes and surface contaminants, it is standard practice to average the spectra from as many as several thousand arcs/sparks that have struck an area as large as 100 square mm in a few seconds of a measurement.

Some OES analyzers are large, non-portable units intended for use in laboratories. Other OES analyzers are "portable," in that they can be moved about. However, prior art "portable" OES analyzers that can identify carbon or other common constituents in iron or steel require two separate components interconnected by a fiber optic/electric cable. For example, an analyzer available from Spectro A. I., Inc. under the trade name Spectroport includes a hand-held probe connected via a 10-foot cable to a suitcase-sized, 33-pound analysis unit. The Spectro iSort analyzer, also from Spectro A. I., Inc., includes a hand-held probe connected by a cable to an analysis unit housed in a 10-pound backpack.

To cover a spectral range required to detect carbon, phosphorous, sulfur and other elements necessary to identify common materials, such as cast iron and various alloys, these prior art analyzers include fixed-wavelength detectors in the hand-held probes for carbon, phosphorous, sulfur and iron, as well as a spectrometer in the analysis unit for other elements. This awkward, two-part structure makes these analyzers difficult to use and move about.

An two-part analyzer available from Metorex, Ewing, N.J., under the trade name ARC-MET 8000 MobileLab, includes a hand-held "probe" connected by a ten-foot cable to a roll-around "main unit." The probe contains a spectrometer with an advertised spectral range of 175-370 nm; however, the roll-around main unit is required to provide power and cooling to the probe and to analyzes the output from the spectrometer. At least some users would prefer to use a hand-held OES analyzer that is fully self-contained.

The Spectrosort analyzer, also from Spectro A. I., Inc., is a one-piece, battery-powered, hand-held analyzer. However, spectral limitations of the spectrometer in this analyzer make it incapable of detecting carbon, phosphorous and sulfur, thus severely limiting the utility of this analyzer.

Users of self-contained, hand-held OES analyzers would prefer analyzers that are capable of detecting carbon and other key elements, so the analyzers can identify a wide range of common materials. However, various roadblocks have thus far prevented construction of such a full-range, self-contained, hand-held analyzer. Among these roadblocks is an inability to construct a spectrometer that exhibits the wavelength range and temperature stability needed for the above-described analysis under typical environmental conditions, in a size and weight appropriate for a hand-held analyzer,

SUMMARY OF THE INVENTION

An embodiment of the present invention provides an analyzer for analyzing composition of a portion of a sample. The analyzer includes a hand-held, self-contained, test instrument. The test instrument includes an exciter for exciting the portion of the sample, the excitation producing an optical signal and a first dispersive element disposed within the hand-held instrument for receiving the optical signal and creating an intermediate optical signal dispersed in a first plane. A second dispersive element disposed within the hand-held instrument disperses the intermediate optical signal so as to place a first resolved optical order on a corresponding first plurality of detector elements and a second resolved optical order on a corresponding second plurality of detector elements. A processor is coupled to receive signals from the first and second pluralities of detector elements and is programmed to process the signals. A battery powers the exciter and the processor.

At least one of the optical orders placed on the corresponding plurality of detector elements may extend to wavelengths shorter than about 193 nm, or shorter than about 178 nm, or at least as short as about 170 nm.

Each plurality of detector elements may be configured so as to receive a continuous spectral range of the resolved optical order placed on the plurality of detector elements. The spectral range placed on the first and second pluralities of detector elements may extend at least from about 178 nm to about 400 nm.

The instrument may include a structure defining an aperture, through which the intermediate optical signal passes. The optical signal may be focused on the structure.

The exciter may include an electrode for sustaining an electrical potential with respect to the portion of the sample and a voltage supply for establishing the electrical potential on the electrode with respect to the portion of the sample. The exciter may include a laser.

The first dispersive element may be a cross-dispersing prism. The second dispersive element may be a diffraction grating, which may be a holographic diffraction grating blazed to provide comparable efficiencies in the first and second resolved optical orders.

The first plurality of detector elements may be not co-planar with the second plurality of detector elements. The test instrument may further include a mirror in an optical path of one of the first and second resolved optical orders, between the second dispersive element and the corresponding plurality of detector elements.

The first and second dispersive elements and the first and second pluralities of detector elements may be rigidly coupled to a carbon-filled polymer structural member, which may include polyphylene sulfide filled with graphite, such as with at least about 40% graphite.

The processor may be programmed for automatic wavelength calibration, based on observed spectral features.

The second dispersive element may provide a resolving power of at least about 5,000 or at least about 10,000.

The instrument may further include a display screen coupled to the processor. The display screen may be a hinged display screen.

An embodiment of the present invention provides an analyzer for analyzing composition of a portion of a sample. The analyzer may include a hand-held, self-contained, test instrument that includes an exciter for exciting the portion of the sample. The excitation produces an optical signal. The instrument also includes a spectrometer having a spectral range extending at least from about 178 nm to about 400 nm disposed in the analyzer to receive the optical signal and operative to disperse the optical signal and produce an output signal from the dispersed optical signal. The instrument also includes a processor coupled to the spectrometer and programmed to process the output signal and a battery powering the exciter, the spectrometer and the processor.

The spectrometer may include a pixilated sensor, and the spectrometer may have a resolution of at least about 0.02 nm per pixel at about 190 nm.

The spectrometer may include a holographic diffraction grating having comparable efficiency in at least two different orders and sensors arranged to receive two orders of the dispersed optical signal from the grating. The spectrometer may be cross-dispersed.

The spectrometer may include a structural member that includes a carbon-filled polymer, to which optical elements of the spectrometer are mounted.

The processor may be programmed to automatically wavelength calibrate the spectrometer, based on observed spectral features.

Another embodiment of the present invention provides a method for analyzing composition of a portion of a sample. The method includes exciting the portion of the sample, thereby producing an optical signal and generating a spectrum from the optical signal. A first predetermined spectral feature is matched with at least a portion of the spectrum. A wavelength is associated with a pixel, based on a location of the first predetermined spectral feature, relative to the pixel. The spectrum is analyzed to determine at least one constituent of the portion of the sample.

Wavelengths may be associated with other pixels, based on an expected linear spectral dispersion over a set of pixels.

A second predetermined spectral feature may be matched with at least a portion of the spectrum and wavelengths may be associated with other pixels, based on a location of the second predetermined spectral feature, relative to the location of the first predetermined spectral feature.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

In accordance with embodiments of the present invention, methods and apparatus are disclosed for analyzing composition of a sample with a hand-held, self-contained, battery-powered test instrument. A spectrometer in the test instrument has a wavelength range broad enough to enable the test instrument to detect and determine relative quantities of carbon, phosphorous, sulfur, manganese, silicon, iron and other elements necessary to identify common alloys. The test instrument's design and construction enables the test instrument to produce accurate results over a wide ambient temperature range, without heating or cooling the spectrometer, thereby conserving power and extending the amount of time the test instrument may be operated before the battery needs to be recharged.

The test instrument excites at least a portion of a sample, thus producing an optical signal. As a result of optical emissions at wavelengths characteristic of elements in the sample, the optical signal contains information that identifies the elements in the sample. The spectrometer wavelength-disperses the optical signal onto a set of sensors, each of which receives a narrow range of wavelengths of the optical signal. A processor is programmed to receive and process signals from the sensors and to identify and quantify the elements in the sample.

A hand-held, self-contained, battery-powered test instrument should be small, light-weight and consume little electrical power. Disclosed embodiments of the present invention enable construction of spectroscopy-based analytical test instruments that exhibit these properties. These embodiments are discussed in the context of analytical techniques and test instruments that employ optical emission spectroscopy (OES); however, the teachings of this application are applicable to other types of analytical test instruments that employ spectral analysis, including test instruments that employ optical absorption spectroscopy. Furthermore, although the disclosed embodiments are discussed in the context of arc/spark excitation, other forms of excitation, including laser-induced breakdown (LIB) and glow discharge (GD) may be used.

General Structure of One Embodiment

Figure 1:
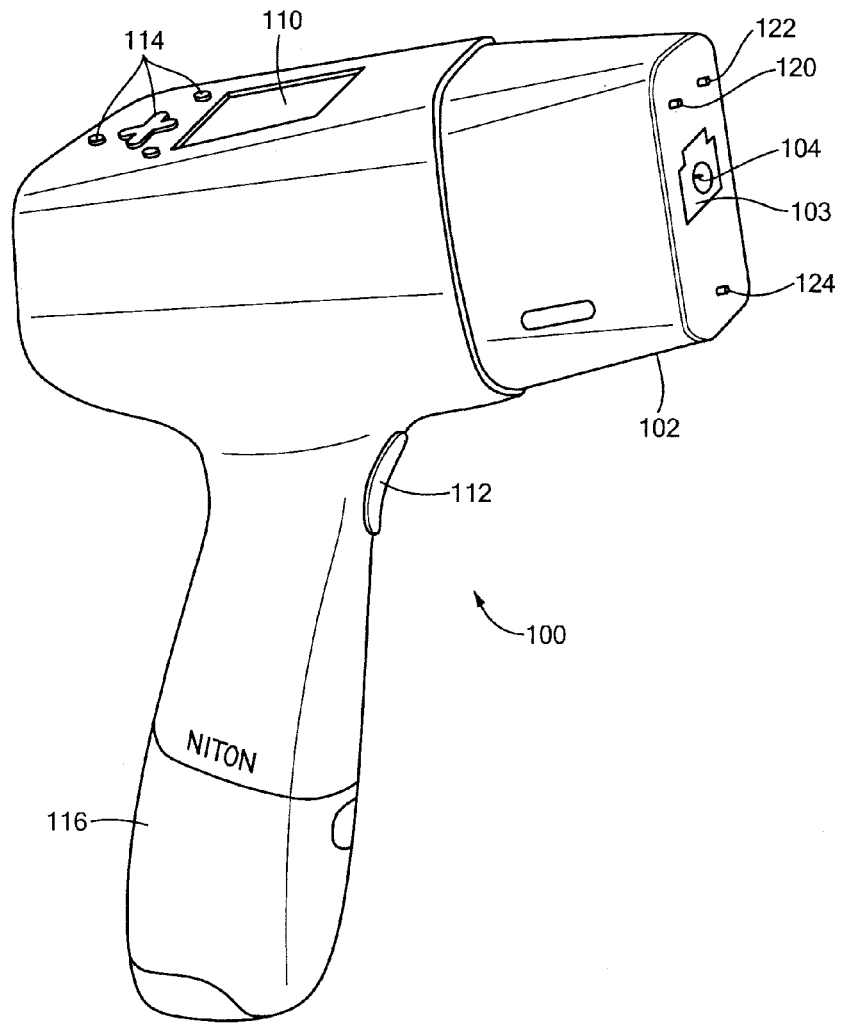
FIG. 1 is a perspective view of a hand-held, self-contained, battery-powered OES test instrument, according to an embodiment of the present invention.

FIG. 1 is a perspective view of a hand-held, self-contained, battery-powered OES test instrument 100, according to one embodiment of the present invention. The instrument 100 includes a snout 102. In operation, an electrically-conductive flat portion 103 of the snout 102 is pressed against an electrically-conductive sample surface (not shown). A spark from a counterelectrode 104 to the sample excites a portion of the sample, thereby producing an optical signal. The counterelectrode 104 is electrically insulated from the electrically conductive flat portion 103 of the snout 102, such as by an insulated disk (not visible). The optical signal enters an upper port (not visible) and is reflected by one or more mirrors (not visible) into a spectrometer 204 inside the instrument 100. A processor (not visible) is coupled to a set of detectors (not visible) in the spectrometer. The processor is programmed to process signals from the detectors. The processor analyzes at least a portion of the spectrum produced by the spectrometer to identify and quantify the elemental composition of the sample.

The processor displays results of the analysis on a touchscreen 110. Optionally, the processor may transmit results of the analysis to an external device, such as a computer or display, via a wired or wireless connection (not shown). The touchscreen 110, a trigger 112 and operator interface buttons 114 enable a user to interact with the processor. A detachable, rechargeable battery 116 powers the processor, touchscreen 110, spectrometer 204 and a spark generator (not visible) that is coupled to the counterelectrode 104.

Figure 2:
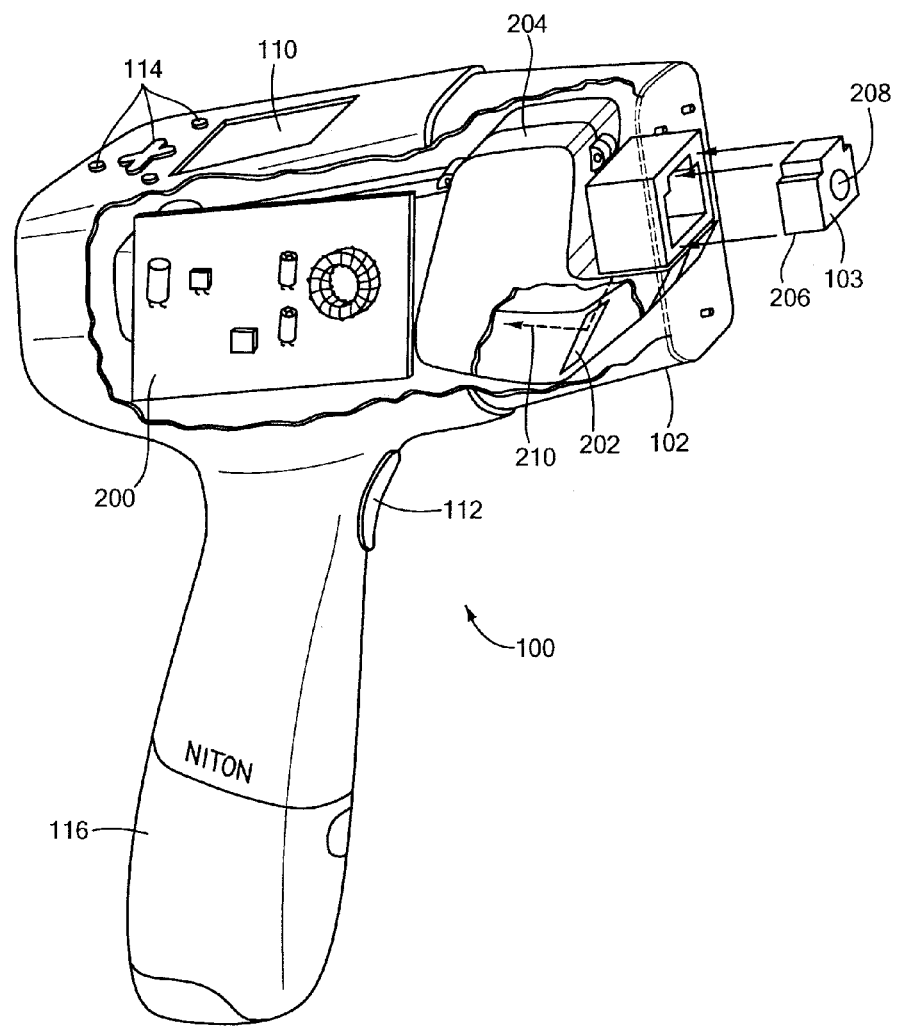
FIG. 2 is a cut-away view of the test instrument of FIG. 1.

FIG. 2 is a cut-away view of the test instrument 100 showing the spark generator 200, a first mirror 202 and the spectrometer 204. The mirror 202 may be an aluminized front-surface mirror with a magnesium fluoride coating and a fused silica substrate, although other suitable mirrors may be used. The mirror 202 may be planar, although a concave (including hyperbolic or parabolic) shape may provide better image quality.

An electrically conductive insert 206 defines a bore 208, in which the counterelectrode 104 (not shown in FIG. 2) is disposed. The insert 206 also provides at least part of the electrically conductive flat portion 103 of the snout 102. The spark generator 200 is electrically connected to the counterelectrode 104 and to the electrically conductive flat portion 103 of the snout 102 to complete on an electrical return circuit with the sample, when the flat portion 103 of the snout 102 is brought into contact with the sample. Much of the snout 102 may be metal or another heat-conductive material to dissipate heat from the spark and from the spark generator 200. A dashed line 210 schematically illustrates a portion of a light path (largely hidden within the snout 102) taken by the optical signal from the vicinity of the counterelectrode 104 to an entrance slit of the spectrometer 204.

Figure 3:
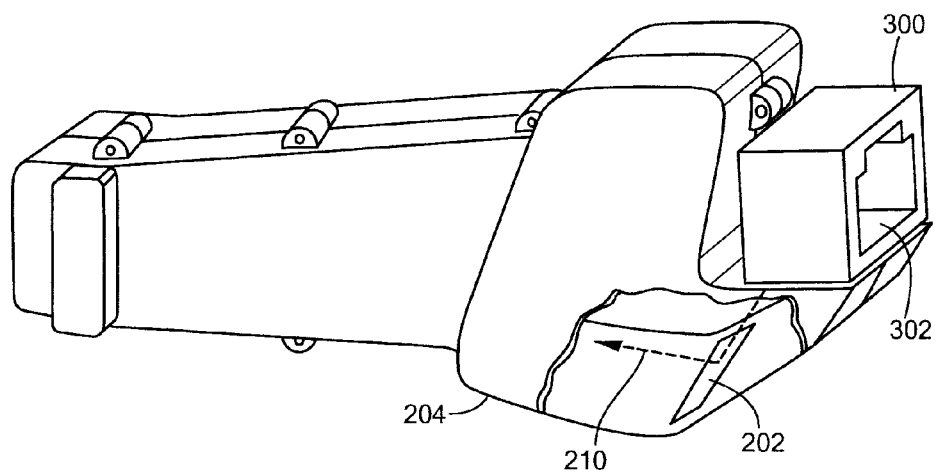
FIG. 3 is a perspective view of a spectrometer of the instrument of FIG. 1, according to an embodiment of the present invention.
Figure 4:
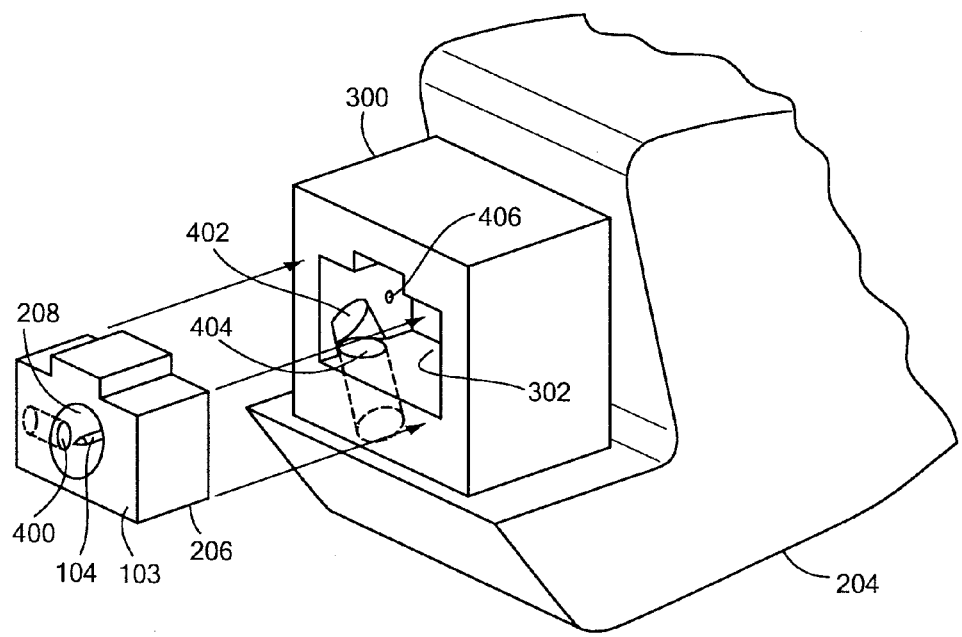
FIG. 4 is a close-up perspective view of a portion of the spectrometer of FIG. 3.

FIG. 3 is a perspective view of the spectrometer 204. The spectrometer 204 housing includes a structure 300 that defines an opening 302, into which the insert 206 (not shown in FIG. 3) in inserted. FIG. 4 is a close-up perspective view of a portion of the spectrometer 204 showing the structure 300 and the insert 206 in more detail. The insert 206 defines a bore 400 through a wall of the insert 206, as shown by dashed lines. The optical signal produced by the sample passes through the bore 400 and is reflected by a second mirror 402 in the structure 300. The second mirror 402 reflects the optical signal via a second bore 404 through the structure 300 to the first mirror 202 (not shown).

A third bore 406 in the structure and a corresponding bore (not visible) in the insert 206 provide a fluid communication path through which a gas may be plumbed to the vicinity of the counter electrode 104 to purge the vicinity of the counterelectrode 104 of air, at least in part because the air may attenuate or block some or all wavelengths of interest in an optical signal. A window (not shown) mounted in the bore 404 provides a gas-tight seal to prevent the gas from escaping from the bore 208 into the spectrometer 208. The window is preferably made of beta alumina ($\beta$-$Al_2O_3$ or "synthetic sapphire") or another material that is sufficiently transparent at the wavelengths of the optical signal.

Environment

As shown in FIG. 3, a sharpened tip portion of the counterelectrode 104 is disposed about 2-3 mm from the sample surface 500, thereby creating an analytical gap. The counterelectrode 104 may be about 1/16-1/4 inch in diameter. The counterelectrode 104 is preferably made of thoriated tungsten, although other suitable materials, such as carbon (graphite) or silver may be used. The counterelectrode 104 should be made of a material that produces a simple spectrum if excited, or at least a spectrum that is easily distinguished from spectra produced by likely materials in the sample 500.

An inert gas, such as argon, may be plumbed via the bore 406 to flood the analytical gap with the gas. Methods and apparatus for providing a gas to a hand-held test instrument, including from a gas tank coupled directly to, and possibly enclosed within a portion of, the instrument, are disclosed in detail in Provisional Patent Application No. 60/889,465, filed Feb. 12, 2007, titled "Small Spot X-Ray Fluorescence (XRF) Analyzer," the contents of which are incorporated by reference as if fully set forth herein. A gas that is not chemically reactive with likely materials in the sample 500, and that produces a relatively simple emission spectrum when excited (or at least a spectrum that is easily distinguished from spectra produced by likely materials in the sample 500), should be selected.

Spark Generation

An electrical potential between the counterelectrode 104 and the sample surface 500 breaks down the gas, enabling an electrical current, in the form of a spark or an arc or both, to flow from the counterelectrode 104 to the sample surface 500. The spark heats the gas and vaporizes a small amount of the sample. The vaporized sample material is excited by the hot gas and produces an optical (although possibly invisible) discharge.

Positive unidirectional current should be provided to the counterelectrode 104 to prevent eroding the counterelectrode 104. The spark generator 200 includes a diode 508 (or an equivalent circuit) to provide an appropriate unidirectional current to the counterelectrode 104. The counterelectrode 104 may be cleaned of debris buildup with a wire brush or by reversing the current and producing sparks/arcs to a sacrificial cleaning sample.

In operation, a series of sparks/arcs may be generated in rapid succession. Each spark may strike a slightly different location on the sample surface 500, due to pitting of the sample surface 500 by the sparks, imperfections and inclusions in the sample surface 500, etc. In general, a high spark repetition rate causes the sparks to strike the sample surface over a smaller area than a low spark repetition rate causes. Thus, it is possible to control the sample area by controlling the spark repetition rate. At about 50 to 400 sparks per second, the sparks strike an area about 3 mm in diameter, whereas at about 1,000 to 2,000 sparks per second, the discharge area is about 1 mm in diameter. It may be desirable to avoid small discharge areas, such as 1 mm in diameter, at least in part because most metals are not sufficiently homogeneous to yield accurate results when only such a small area is tested. Sampling such a small area may produce a result that is biased by the composition of the small area.

Figure 6:
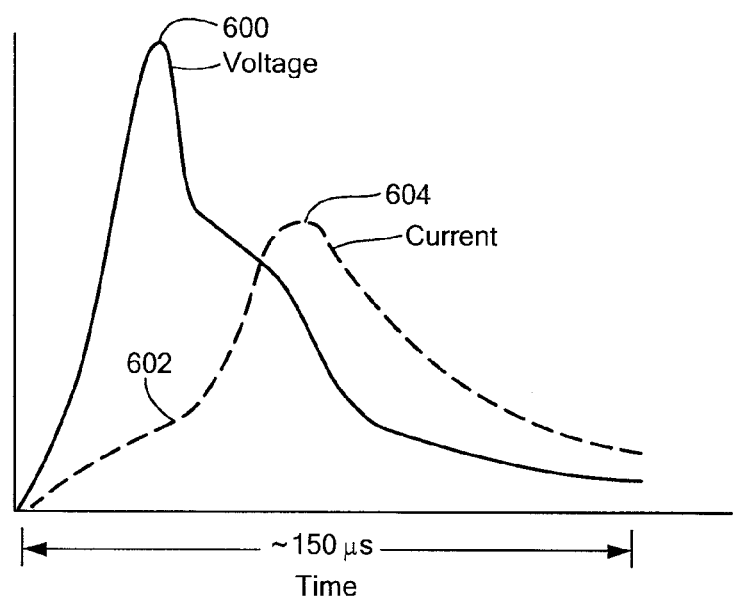
FIG. 6 is a graph showing representative voltage and current curves plotted against time for a single spark/arc generated by the instrument of FIG. 1, according to one embodiment of the present invention.

Voltage and current (versus time) profiles (waveforms) of a signal provided to the counterelectrode 104 to produce the spark/arc should be controlled to optimize initiating the spark, vaporizing the sample and heating the gas, while limiting power consumption. FIG. 6 is a graph showing representative voltage and current curves plotted against time for a single spark/arc. As shown in the graph, a short-duration, high-voltage peak 600 initiates a spark to breakdown the gas in an analytical gap between the counterelectrode 104 and the sample surface 500. The spark erodes a portion of the sample into the analytical gas. Thereafter, the voltage is reduced. The spark is a low-current spark, as indicated in a portion 602 of the current graph. However, thereafter the current is increased and reaches a peak 604 while the voltage is moderately high to sustain an arc to excite the eroded sample material in the analytical gap. The excited material emits an optical signal characteristic of the elemental composition of the excited material. Thereafter, the current and voltage are reduced. Due to the varying amounts of power introduced into the analytical gap over the course of the spark/arc, the temperature in the analytical gap varies over the duration of the spark/arc.

Figure 7A:
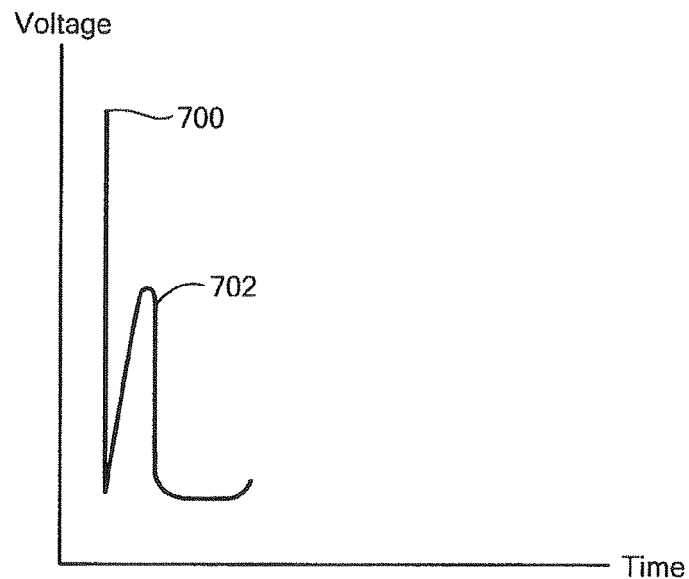
FIG. 7 contains two graphs showing representative voltage and current curves plotted against time for sparks/arcs generated by the instrument of FIG. 1, according to one embodiment of the present invention.
Figure 7B:
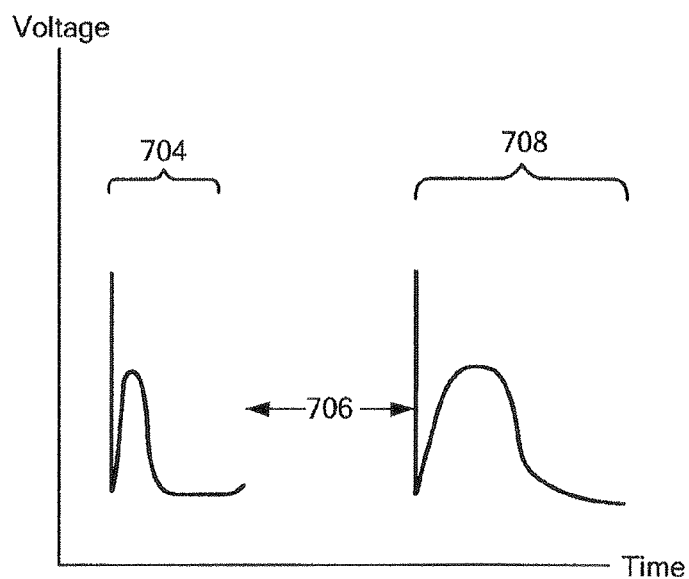

For analyzing hard metals, such as iron and nickel, a voltage profile as shown in the top graph (A) of FIG. 7 may be used. The voltage profile shows a high-energy pre-spark 700, followed by a high-current, but lower voltage, arc 702. For analyzing soft metals, such as aluminum, magnesium or copper, a two-phase voltage profile as shown in the bottom graph (B) of FIG. 7 may be used. The voltage profile shows a spark portion 704, a delay 706 and a separate arc portion 708. The spark portion 704 may be used to determine the primary alloy in a sample, and the arc portion 708 may be used to determine trace elements in the sample. In general, the voltage of the signal in the lower graph (B) is less than the voltage of the signal in the upper graph (A).

In one embodiment, the initial breakdown voltage is about 6,000-10,000 volts, as required to break down the argon or other gas in the analytical gap. In one embodiment, the peak current is about 60-100 amps. The absolute values of the voltages and currents are not as important as repeatability of the voltages and currents from spark/arc to spark/arc and avoiding ringing in the signal to the counterelectrode 104. The amplitudes and profiles of the voltages and currents should be as repeatable as practical.

The spark generator 200 operates under the control of the processor. That is, the processor may specify a repetition rate, as well as voltages, currents and/or profiles, to the spark generator 200. Alternatively, the voltages, currents and/or profiles may be pre-configured in the spark generator 200. The spark generator 200 may be any suitable circuit, such as a switched-mode power supply (SMPS), such as high-power thyristor or MOSFET circuit, that produces voltages and currents as described above.

To prevent accidental exposure of a user to spark voltage, the snout 102 may include one or more momentary contact switches, pressure transducers or other sensors that must be activated by a sample surface before the spark generator 200 produces a spark signal. One embodiment of such a safety interlock system is shown in FIG. 1. Three momentary contact switches 120, 122 and 124 are mounted in the snout 102, such that the switches 120-124 are activated only if the flat portion 103 of the snout 102 is fully engaged against the surface of a sample.

Light Collection

Figure 5:
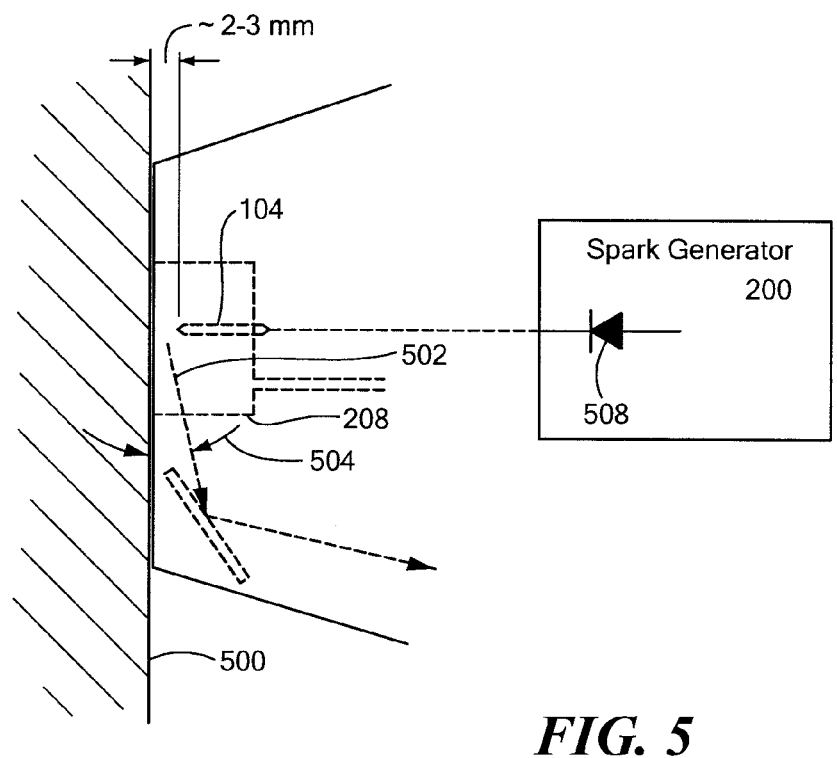
FIG. 5 is shows a snout of the test instrument of FIG. 1 in contact with a sample surface.
Figure 8:
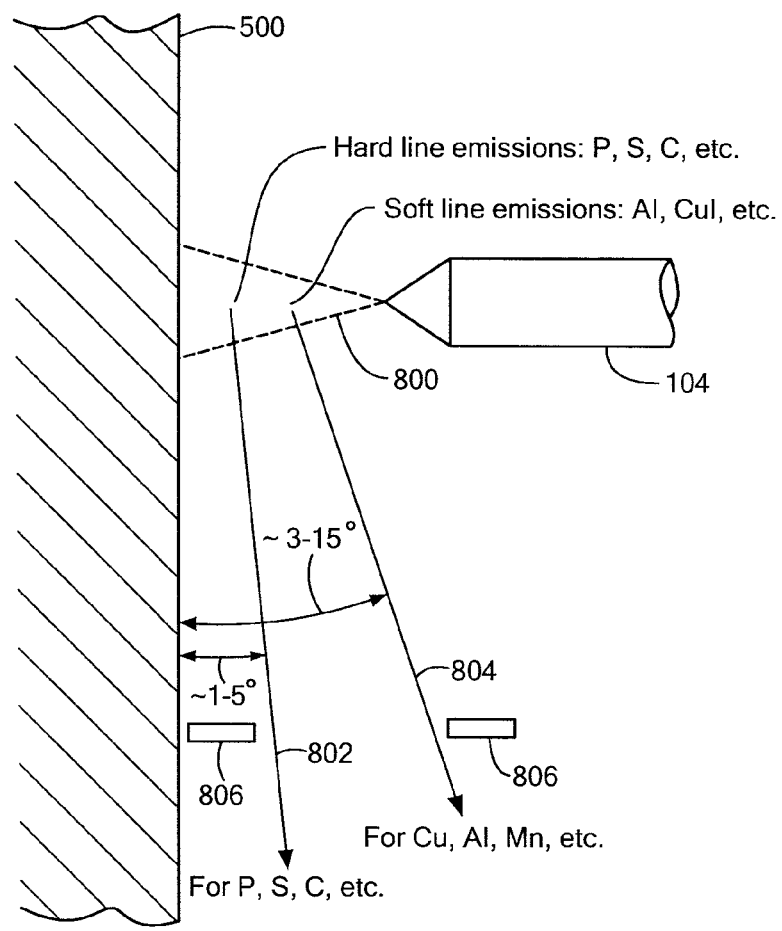
FIG. 8 is a close-up schematic view of an analytical gap produced by the test instrument of FIG. 1.

Referring back to FIG. 5, it should be noted that the light path 502 forms an angle 504 with the sample surface 500. FIG. 8 is a close-up view of the analytical gap, showing a discharge region 800 between the counterelectrode 104 and the sample surface 500. The portion of the region 800 closer to the sample surface 500 is hotter (at about 30,000° C.) than the portion of the region 800 (at about 1,500° C.) closer to the counterelectrode 104. Thus, hard line emissions 802 from elements such as phosphor, sulfur and carbon emanate from the hotter portion of the region 800. Conversely, soft line emissions 804 from elements such as aluminum and copper emanate from the cooler portion of the region 800.

Emissions from an analyte should be sampled from a volume of the analytical gap where the analyte is ionized. The hard line emissions 802 should be observed at an angle of about 1-5°, whereas the soft line emissions 804 should be observed at an angle of about 3-15°. An angle of about 3° provides a good compromise, enabling observation of both the hard line emissions 802 and the soft line emissions 804. Referring again to FIG. 5, the angle 504 may be about 3°, although other small angles may be used. In addition, multiple optical paths, possibly each at a different angle, may be provided from the analytical gap and recombined closer to the spectrometer 204. A mask 806 should be used to avoid observing emissions from the hot tip of the counterelectrode 104 or emissions from the sample surface 500.

As noted above, a combination of high-energy and low-energy sparks and/or arcs may be used in a series of excitations, facilitating detecting hard metals and soft metals in a sample during different sparks/arcs. In one embodiment, the major element(s) in the sample is(are) analyzed with a first pulse, and trace elements in the sample are analyzed with a second pulse.

Emissions from some elements peak later during a spark/arc than emissions from other elements. Similarly, "background" emissions, such as from the sample surface 500 or the tip of the counterelectrode 104, may peak earlier than emissions from some of the elements in the sample. For example, emissions from lead peak late, after many of the background emissions have subsided. Time-resolved analysis of the optical signal may provide a better signal-to-noise ratio by analyzing the spectrum for emissions from particular elements when those emissions peak. Time-resolved analysis of an optical signal is discussed in detail in provisional patent application No. 60/891,320, filed Feb. 23, 2007, titled "Time-Resolved Spectroscopy with Sensor Array" and in U.S. patent application Ser. No. 12/035,477, by Denis Baiko, et al, titled "Fast and Precise Time-Resolved Spectroscopy with Linear Sensor Array," filed Feb. 22, 2008, the contents of which are incorporated by reference as if fully set forth herein.

Spectrometer

Maintaining physical relationships, such as distances and orientations, among optical components of a spectrometer is necessary to maintain accuracy of the spectrometer. In a traditional spectrometer, the optical components, such as a structure defining an entrance slit, a diffraction grating and one or more sensors, are rigidly mounted to a structural member made of cast iron or Invar (FeNi), and the spectrometer is temperature controlled to limit thermal expansion or contraction of the structural member. Temperature control is traditionally achieved by heating the spectrometer to a uniform and constant temperature, although some spectrometers are cooled, rather than heated. In either case, energy is consumed to heat or cool the spectrometer. Sometimes electric fans are used to circulate air within or around a spectrometer to maintain a uniform temperature. Heating a spectrometer may necessitate selecting temperature-insensitive sensors or cooling sensors within the spectrometer to avoid generating heat-induced noise in the sensors.

Figure 9:
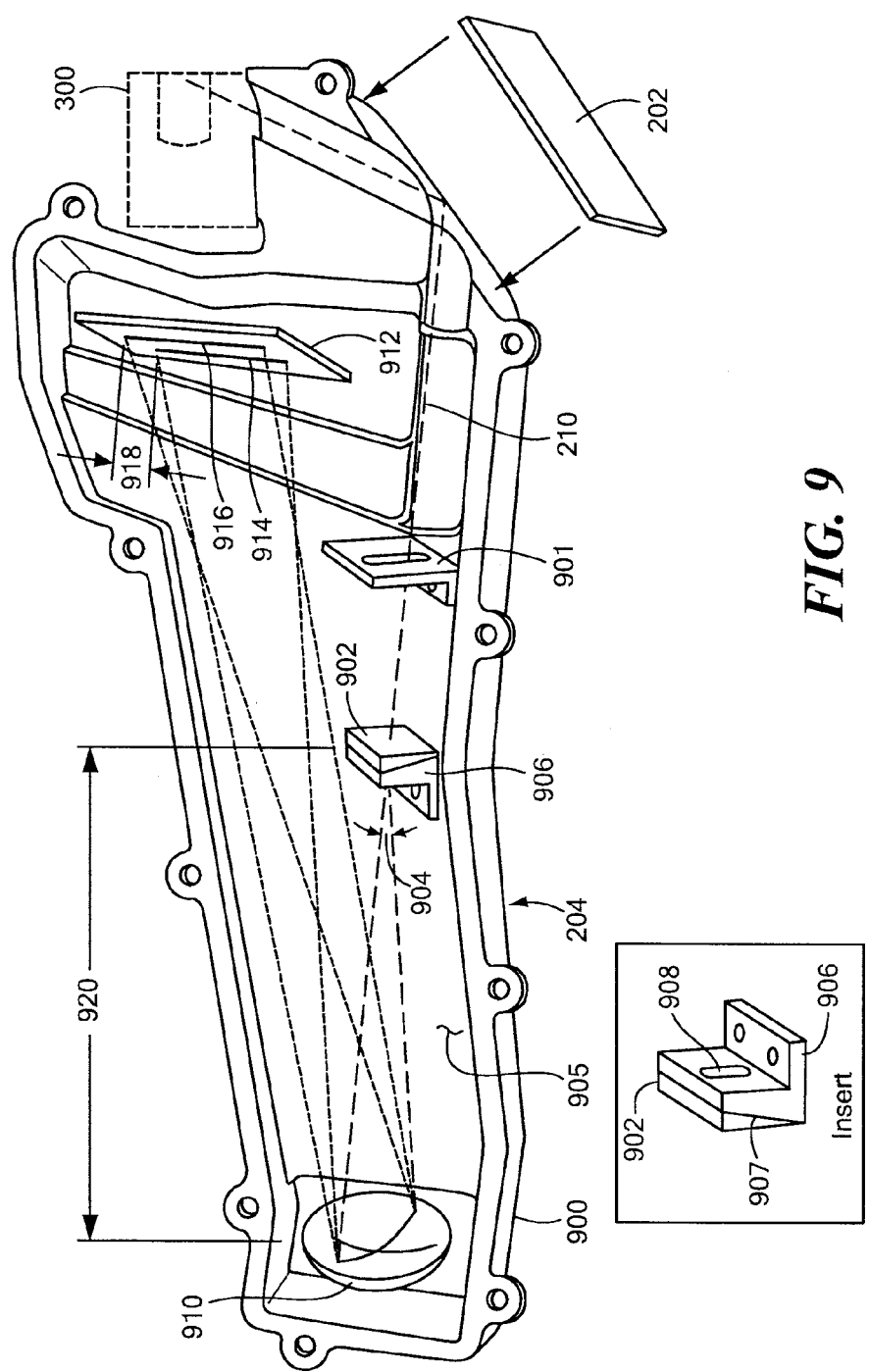
FIG. 9 is a cutaway perspective diagram of the spectrometer of FIGS. 3 and 4, according to one embodiment of the present invention.

A spectrometer in a hand-held test instrument should be small, light-weight and consume little electrical power. FIG. 9 is a cutaway perspective schematic diagram (with the cover removed for clarity) of the spectrometer 204, according to one embodiment of the present invention. Various aspects of the spectrometer 204, including its cross-dispersed design, contribute to its compact size, light weight and low power consumption.

Structural components, such as the case 900 and cover (removed for clarity), of the spectrometer 204 are made of a light-weight material, such as graphite-filled polyphenylene sulfide (PPS), that has a small coefficient of thermal expansion (CTE) over a range of expected ambient temperatures in contexts where the test instrument 100 may be used. The small CTE reduces or eliminates the need to temperature-control the spectrometer 204, thereby conserving electrical power, while maintaining the accuracy of the spectrometer 204. In addition, PPS is black, which assists in absorbing stray light within the spectrometer 204. PPS may be machined or injection molded, or a combination thereof, to produce the structural components of the spectrometer 204.

PPS is available from Chevron Phillips, The Woodlands, Tex., under the tradename Ryton PPS. Polyphenylene sulfide filled with about 40% graphite is preferred. Such a material is available under the designation IPC-1834 from Hoerbiger America Rings & Packing, Inc., Houston, Tex. 77023 or under the designation "Bearing Grade" from Boedeker Plastics, Inc., Shiner, Tex. Other polymers, high-carbon composites, glass-filled polymers or liquid crystal polymers that exhibit or are modified, such as by filling with carbon or another suitable filler, for a small CTE at expected ambient temperatures may also be used.

The optical signal 210 is reflected by the mirror 202 onto an entrance slit 901. The entrance slit 901 may be about 5 μm wide. A prism 902 vertically disperses the incoming light, as indicated at 904. The prism 902 is located about 60 mm from the entrance slit 901. The prism 902 is preferably made of beta alumina or another material that is sufficiently transparent at the wavelengths of interest.

The prism 902 is attached to a field stop (internal baffle) 906. The field stop 906 and prism 902 are shown enlarged and from another view in the insert in FIG. 9. The prism 902 should be mounted at its minimum deviation angle to minimize astigmatism. In one embodiment, the prism 902 refracts light at an angle of about 6.8°, thus the prism 902 is tilted at about half that angle, so the axis of the output from the prism 902 (toward the grating 910) is parallel to the floor 905 of the spectrometer case 900. The back 907 of the field stop is angled to tilt the prism 902 appropriately.

The field stop 906 defines an approximately ¼-inch wide aperture 908, through which the vertically-dispersed light passes. As noted, spark strikes on the sample surface 500 occur within a small area, not necessarily at a single point on the surface. To accommodate this spark "wander," the image of the spark is defocused somewhat at the entrance slit 901; instead, the image is focused on the internal baffle 906.

The vertically-dispersed light 904 from the prism 902 impinges on a concave holographic grating 910. The grating 910 is about ½-inch thick and about 50-75 mm in diameter. The internal baffle 906 masks off the edges of the discharge volume in the analytical gap, thus preventing an optical signal from the tip of the counterelectrode 104 or from the sample surface 500 from reaching the grating 910. The grating 910 horizontally disperses the light. The horizontally-dispersed light impinges on an array of sensors 912. The grating 910 is constructed to have comparable efficiencies in two different, although not necessarily consecutive, orders. Each order may be positive or negative.

The grating 910 produces two distinct spectra, which will be referred to as a first-order spectrum 914 and a second-order spectrum 916, on the sensors 912. The resolution of the second-order spectrum 916 may be greater than the resolution of the first-order spectrum 914. Because the prism 902 vertically disperses the incoming light 900, long and short wavelengths of the vertically-dispersed light impinge on the grating 910 at different angles. This angular difference causes a vertical displacement 918 between the first-order spectrum 914 and the second-order spectrum 916 on the sensors 912. In one embodiment, the vertical displacement 918 is about 2 mm. The sensors 912 may include two rows of sensors, one row of sensors for each spectrum 914 and 916, although an alternative embodiment of the sensors 912 is described below.

Order Separation

Figure 10:
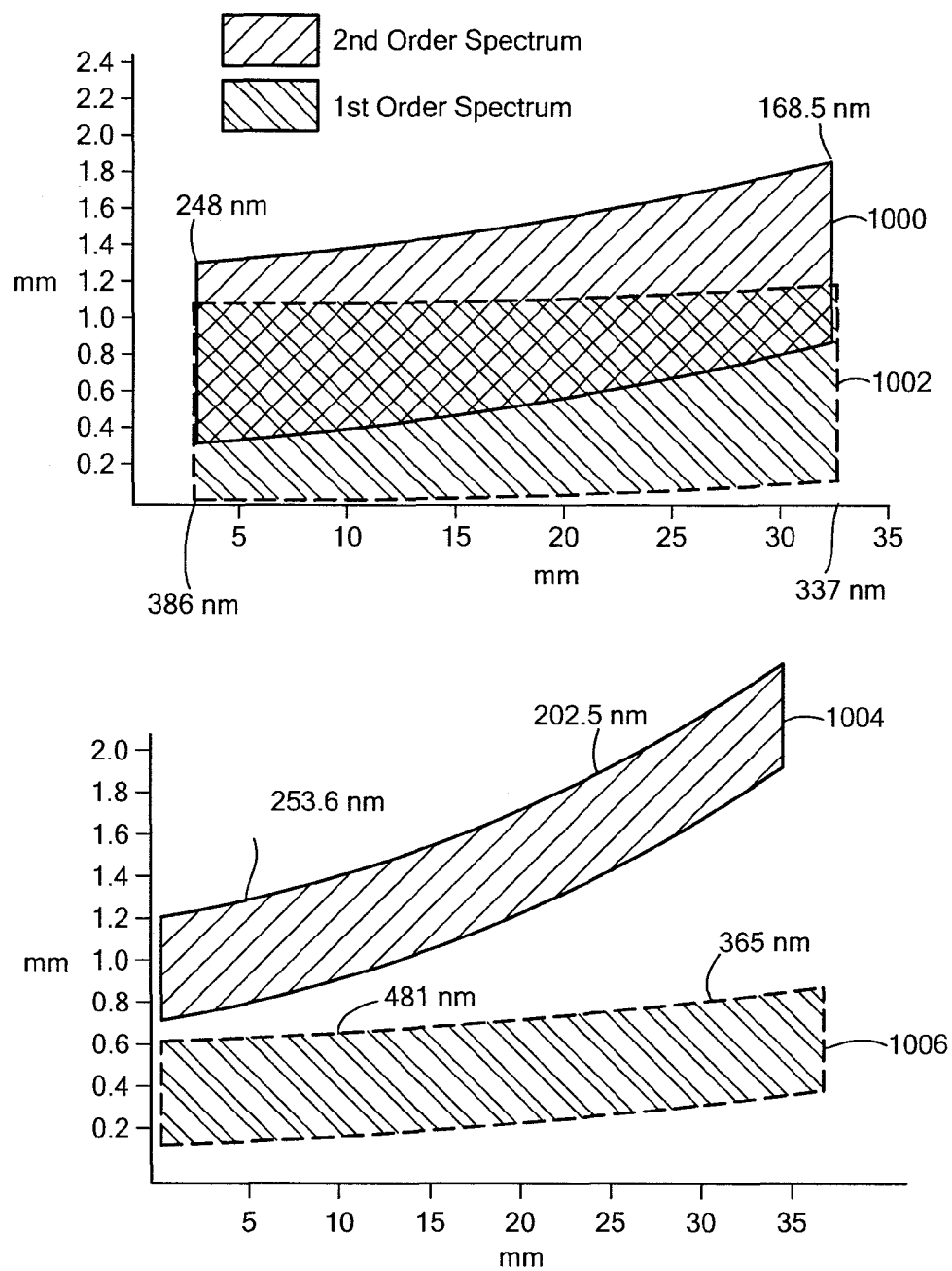
FIG. 10 contains two schematic representations of spectra projected on sensor arrays of the instrument of FIG. 1, in relation to selecting system parameters according to one embodiment of the present invention.

Various system parameters influence the extent of the vertical displacement 918. If an insufficient amount of vertical displacement 918 is provided, the two order spectra 914 and 916 partially or completely overlap each other on the sensors 912. Depending on the heights of the sensor pixels, such an overlap may make it impossible to achieve a clean spectrum on each set of sensors. The upper portion of FIG. 10 schematically represents two order spectra 1000 and 1002, as imaged on the sensors 912 (FIG. 9), in which the two spectra 1000 and 1002 significantly overlap, possibly preventing achieving a clean spectrum on each set of sensors.

Returning to FIG. 9, the amount of vertical displacement 918 between the two spectra 914 and 916 on the sensors 912 depends, in part, on the amount of dispersion 904 caused by the prism 902 which, in turn, depends on the index of refraction of the material of the prism 902 and on the apex angle of the prism 902. However, large apex angles result in thicker prisms, which may further attenuate the optical signal, particularly in the ultraviolet range.

The vertical displacement 918 also depends, in part, on the linear magnification of the focusing system (i.e., on magnification of the convex grating 910), on the distance 920 between the prism 902 and the grating 910 and on the distance between the grating 910 and the sensors 912. The grating 910 is a focusing element, thus decreasing the separation 920 increases the displacement 918. In one embodiment, the linear magnification of the convex grating 910 is about −1.

In one embodiment, the prism 902 is placed as close as possible to the grating 910, without occluding the light path, between the grating 910 and the sensors 912, of any portion of either order's spectrum 914 or 916 that is of analytical interest. Such a placement of the prism 902 in this embodiment creates a slit 901 to prism 902 distance of about 60 mm. The lower portion of FIG. 10 is a schematic diagram of two order spectra 1004 and 1006, as imaged on the sensors 912 (FIG. 9), achieved by positioning a beta alumina prism having an apex angle of about 8° as described above. As can be seen in lower portion of FIG. 10, the two spectra 1004 and 1006 do not overlap and provide a vertical displacement of about 2 mm between the spectra 1004 and 1006, although the displacement may vary with wavelength. In one embodiment, the displacement varies from about 0.6 mm to about 3 mm over the wavelength range of interest.

For identifying ferrous and other common metals, optical emissions from the analytical gap that have wavelengths between about 170 nm and about 410 nm are of interest. In one embodiment, the grating 910 (FIG. 9) is constructed such that the efficiency of the grating at the first order is relatively high for wavelengths between about 247 nm and about 410 nm and relatively low outside this range, and the efficiency of the grating at the second order is relatively high for wavelengths between about 170 nm and about 247 nm and relatively low outside this range, although there may be some overlap between the high-efficiency portions of the first and second orders. The grating 910 design, the cross-dispersion provided by the combination of the prism 902 and the grating 910 and the two rows of sensors 912 enable the spectrometer 204 to analyze a relatively broad range of wavelengths in a relatively small amount of space. In some embodiments, there may be a spectral gap or overlap between the first-order spectrum 914 and the second-order spectrum 916 on the sensors 912.

Figure 11:
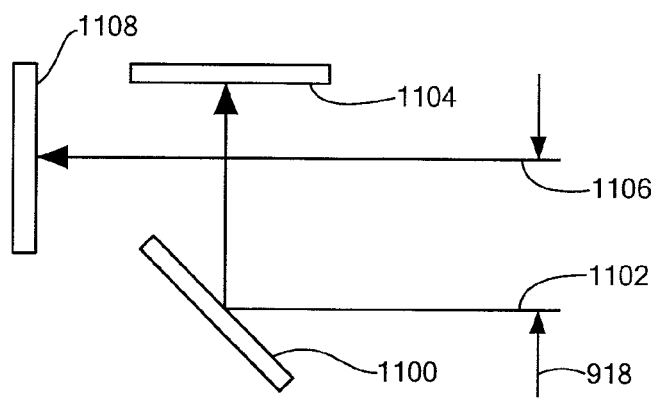
FIG. 11 is a schematic diagram two rows of sensors, according to one embodiment of the present invention.
Figure 12:
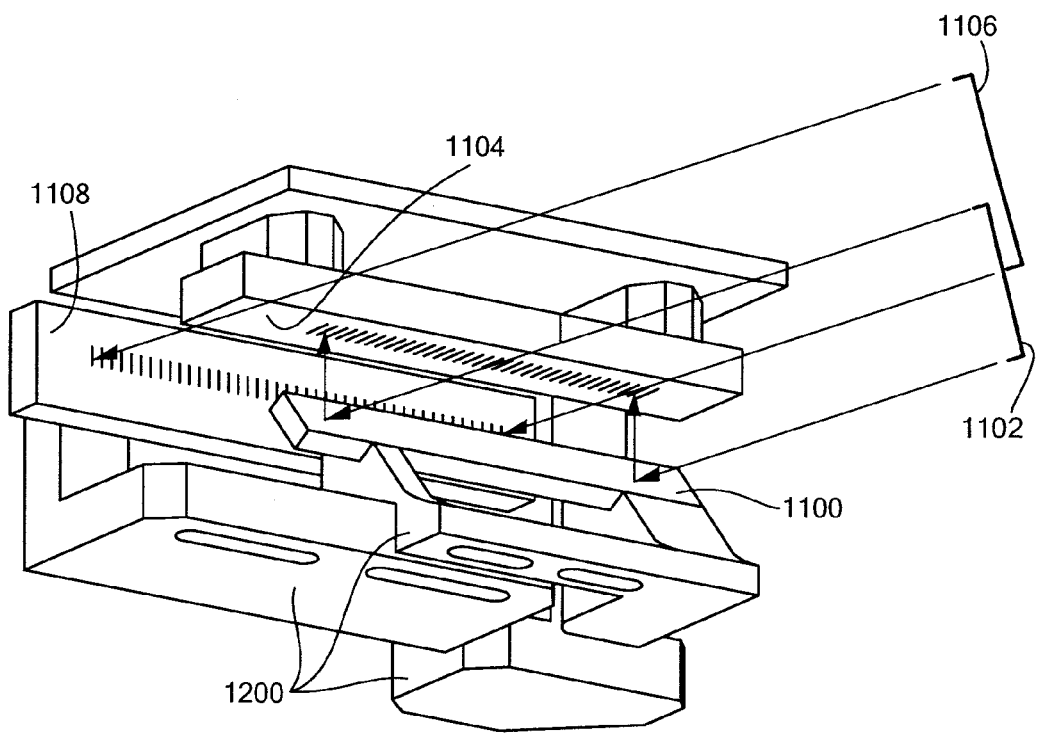
FIG. 12 is a perspective view of the two rows of sensors of FIG. 11 and corresponding mounting brackets therefore, according to one embodiment of the present invention.

The vertical displacement 918 between the first-order spectrum 914 and the second-order spectrum 916 may be insufficient for two co-planar rows of sensors 912. In this case, one of the two rows of sensors may be oriented in a plane that is perpendicular to the sensor array 912 shown in FIG. 9, and a mirror may be used to reflect one of the two spectra onto the perpendicular sensor array. A side view of such an arrangement is shown schematically in FIG. 11, and a perspective view (looking slightly upward and from the side) of such an arrangement is shown in FIG. 12. Referring to FIG. 11, a mirror 1100 reflects first order light 1102 to a downward-facing row of sensors 1104. Second order light 1106 impinges directly, i.e. without first being reflected, on a forward-facing row of sensors 1108. At the wavelengths of interest, mirrors reflect longer wavelengths of light more efficiently than shorter wavelengths. For example, below about 240 nm, about 20% of an optical signal is lost as a result of reflecting the signal with a mirror. The order primarily composed of wavelengths that are less efficiently reflected by a mirror should impinge on the forward-facing row of sensors 1108. As noted, in one embodiment, the second order light (ranging from about 170 nm to about 250 nm) impinges directly on the forward-facing sensors 1108. FIG. 12 shows mounting brackets 1200 used to mount the mirror 1100 and the two rows of sensors 1104 and 1108 to the floor 905 of the housing 900.

Figure 19:
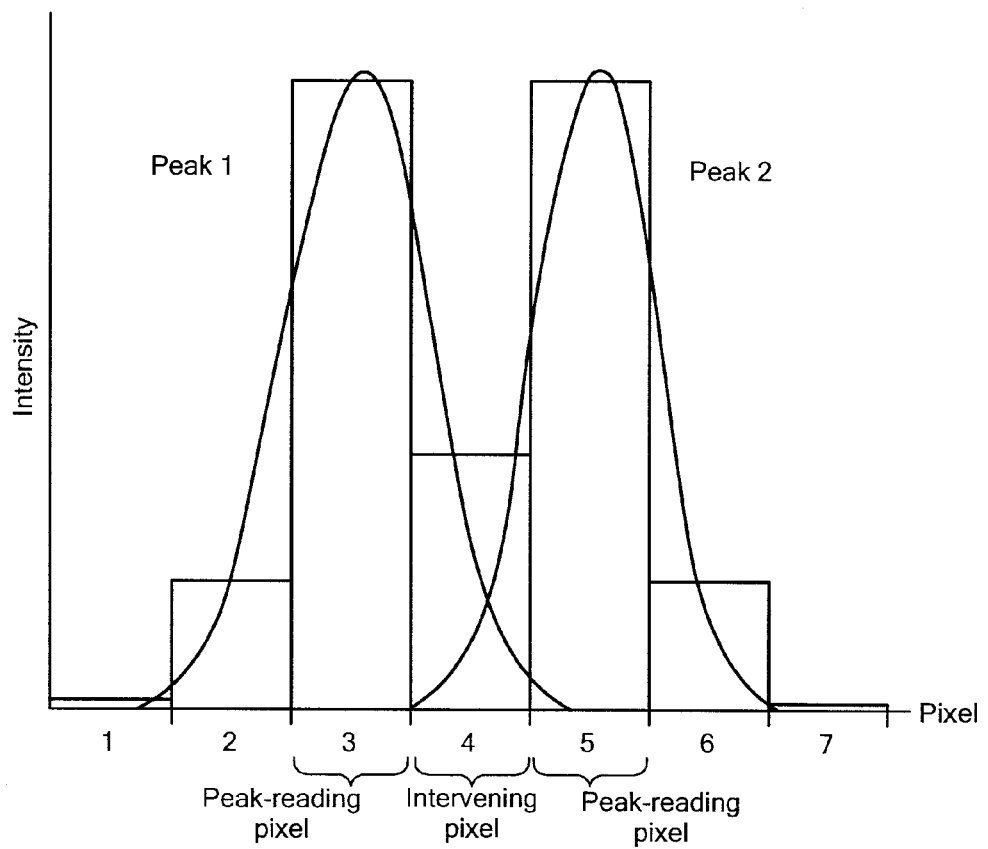
FIG. 19 is a schematic graph illustrating two spectral peaks and corresponding signals produced by sensor pixels.

Spectral resolution is generally defined as the spectral separation between the two closest peaks that a spectrometer can resolve. For a digital sensor that includes a set of adjacent pixels to resolve two peaks, at least one pixel between the two peaks should receive a lower signal than its neighbors, as shown schematically in FIG. 19. If the peaks fall on the sensor so that the pixels with the maximum signals are next to each other, the two peaks may not be resolved by the spectrometer/sensor combination.

Spectrometer bandpass (BP) specifies how much spectral bandwidth is seen at a given wavelength position. Since bandpass limits the ability of a spectrometer to separate peaks, it is common to refer to the BP as the spectral resolution of the spectrometer. The BP may be calculated from the output image width and the reciprocal linear dispersion of the dispersive element in the spectrometer. The reciprocal linear dispersion indicates the width of spectrum that is spread over a distance of 1 mm at the focal plane, i.e., the sensors 912 in the description above. Reciprocal linear dispersion, which varies with wavelength, is given in nm/mm and is typically listed as a primary instrument specification. The reciprocal linear dispersion of the diffraction grating depends largely on the pitch of the grooves in the grating.

In one embodiment of the spectrometer 204, the diffraction grating 910 has a reciprocal linear dispersion of about 5 nm/mm, and the entrance slit 901 has a width of about 5 μm. Thus, in one embodiment, the diffraction grating 910 provides a resolving power of at least about 5,000 and, in another embodiment, at least about 10,000. In one embodiment of the spectrometer 204, each sensor 1004 and 1008 has an effective pixel pitch of about 7 μm. The resulting resolution is about 0.02 nm per pixel in the second-order spectrum 916 and about 0.04 nm per pixel in the first-order spectrum 914.

Figure 21:
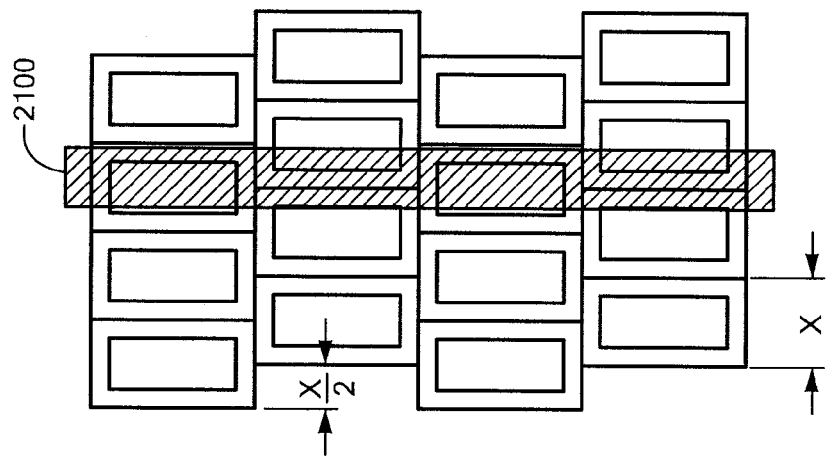
FIGS. 20 and 21 depict two embodiments of staggered pixel structures for a sensor array, in accordance with embodiments of the present invention.
Figure 20:
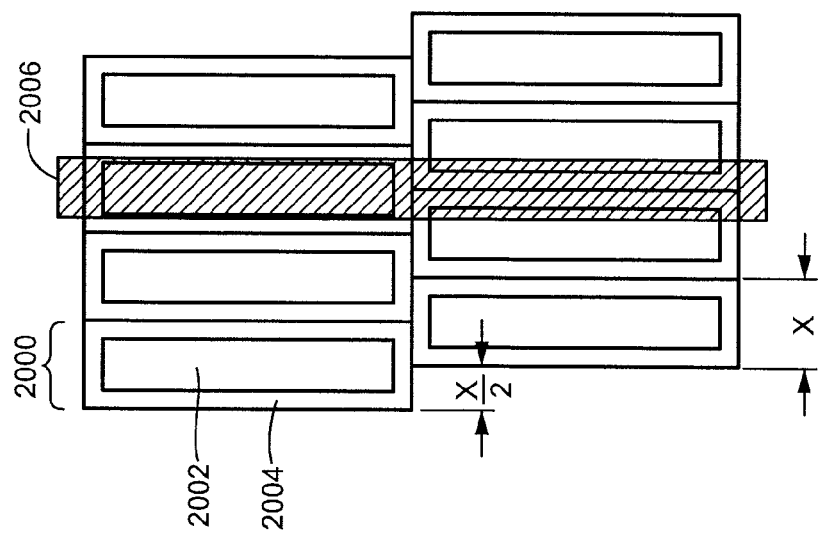

Each sensor 1104 and 1108 may incorporate two or more rows of pixels in which the pixels are staggered horizontally, which increases the effective optical resolution of the device. FIGS. 20 and 21 depict two alternate staggered pixel configurations. A typical pixel 2000 includes a light-sensitive area 2002 and a surrounding light-insensitive area 2004. In a typical spectroscopic application, such as spark OES, the optics are configured to impose a tall narrow slit image 2006 or 2100 onto the detection device. By manufacturing the device with two or more rows of pixels, each with a horizontal resolution of X, where the pixels in the other row(s) are offset by a distance of X/2, the effective resolution of the system improves to X/2. This, in turn, allows for the use of more narrow entrance slits, which effectively improves the spectroscopic resolution of the system.

One embodiment of the present invention operates with uncollimated optical signals provided to the prism 902. Although uncomimated signals may cause a small amount of aberration in the image projected on the sensors 1104 and 1108, any "smearing" of the image is generally in the same direction as the long dimension of the rectangular pixels. Thus, these aberrations do not negatively affect the resolution of the spectrometer. In addition, using lower orders, such as first and second, of diffracted signals from the grating 910 may minimize some aberrations.

The spectrometer described herein may be used in applications other than hand-held analytical instruments. For example, the spectrometer may be used in bench-top analyzers, telescopes, telecommunications equipment, etc.

Dynamic Wavelength Calibration

Figure 22:
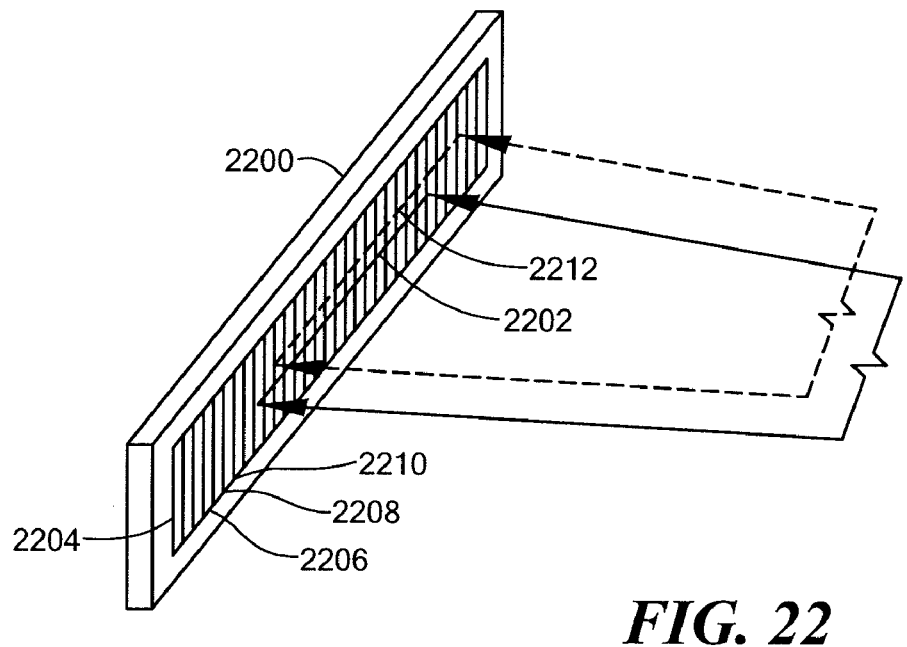
FIG. 22 is a perspective schematic diagram of a sensor and a spectrum and a shifted spectrum impinging on the sensor, according to one embodiment of the present invention.

In one embodiment, each row of sensors 1104 and 1108 contains about 4,096 pixels; however, in other embodiments other numbers of pixels may be used. Sensors that include more pixels than are necessary to image a spectrum may provide advantages. FIG. 22 is a perspective schematic diagram of a sensor 2200 and a spectrum 2202 impinging on the sensor 2200. The sensor 2200 contains a row 2204 of sensor pixels, exemplified by pixels 2206, 2208 and 2210. If the row of pixels 2204 is just wide enough to capture a spectrum of analytical interest, then when the sensor is mounted in the spectrometer, the position of the sensor 2200 (or another component, such as the grating) may need to be carefully adjusted, so the entire spectrum is imaged, i.e., the entire image impinges on the row of pixels 2204.

However, if the row of pixels 2204 is longer than the spectrum 2202 is wide (as shown in FIG. 22), the sensor 2200 may be mounted with less positional precision, as long as the entire spectrum 2202 falls somewhere on the row of pixels 2204. Essentially, the additional pixels, i.e., the number of pixels in excess of the number needed to image the entire spectrum 2202, provide a tolerance, within which the sensor 2200 may be mounted. Once the sensor 2200 is mounted, the sensor 2200 or the processor (not shown) may determine which pixels are illuminated by the spectrum 2202 and, if desired, assign pixel numbers or addresses beginning with the pixel at one end of the spectrum 2202. If the spectrum 2202 shifts position on the sensor 2200, as indicated by spectrum 2212, due to, for example, thermal expansion or contraction of a component of the spectrometer or elsewhere in the instrument, the sensor 2200 or the processor may compensate by renumbering the pixels or reading data from a different set of pixels, corresponding to the location where the spectrum 2212 has shifted.

In one embodiment, the optical system and sensor is configured such that the sensor detects a first order spectrum that extends from about 246.9 nm to about 410 nm, and the sensor detect a second order spectrum that extends from about 170 nm to about 246.9 nm. There should be some overlap between the two spectra at, for example, 246.9 nm.

The row of pixels 2204 may be wavelength calibrated, i.e., the pixels may be associated with wavelengths, by testing a sample that has a known composition and correlating expected peaks in the spectrum with pixels that experience correspondingly high values of illumination. In one embodiment, the processor automatically wavelength calibrates the row of pixels 2204 by matching an observed spectral feature with one of a set of stored feature prototypes. Essentially, the processor matches the pattern of the observed feature with a known pattern.

Figure 23:
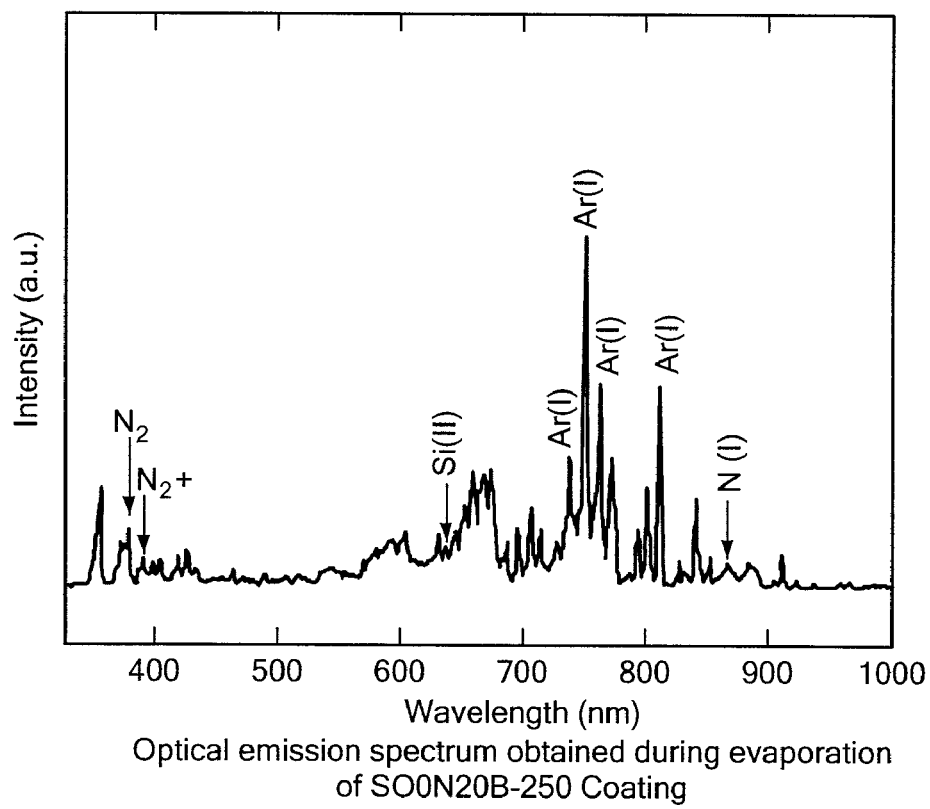
FIG. 23 is a graph illustrating a known spectrum.

The pattern may include relative spacing between or among peaks, valleys or other spectral characteristics and relative height(s) of the peak(s), valley(s), etc. For example, FIG. 23 illustrates a known spectrum. The spectrum contains well-defined peaks for various elements. One or more stored feature prototypes are stored in a memory accessible by the processor. The feature prototypes need not include information about an entire spectrum of a material; the prototype may include information about only selected peaks, etc.

Prototypes may be based on expected "matrix" elements in expected samples, because these elements will likely have a strong presence in every sample exposure. For example, for iron and steel samples, a prototype that contains information about elemental iron (Fe) may be used, and for aluminum alloys, a prototype that contains information about elemental aluminum (Al) may be used.

After the instrument takes a reading, the processor searches the data provided by the sensors for a match with one or more of the stored prototypes. Note that the data from the sensor may include signatures of additional materials that are included in the tested sample, but are not represented in the prototypes. The prototypes may be chosen so that their patterns are easily detected among other likely materials in samples. For initial wavelength calibration, a known standard may be used as the sample.

Once the processor identifies a prototype pattern that matches observed data, the processor associates one or more pixels, where one or more features of the prototype are observed, with corresponding wavelength(s) stored with the prototype data. In one embodiment, the processor associates a wavelength or wavelength range to one pixel, according to an observed and matched feature, and assigns other wavelengths or ranges to the other pixels based on an expected linear spectral dispersion based on the geometry of the spectrometer.

In another embodiment, the processor associates a wavelength or range to a pixel, as described above, and calculates an actual linear spectral dispersion observed on the sensor, based on relative spacing between or among observed and matched features, and associates wavelengths or ranges with other pixels, based on the calculated linear spectral dispersion.

The wavelength calibration may create a mapping between pixel number and wavelength. The dispersion is not necessarily constant across the length of the detector. Thus, identifying more peaks allows for a higher order mapping function to be used. For example, identifying one peak allows for a 0th order "shift" correction, two peaks allows for a 1st order linear correction, and so on.

Figure 24:
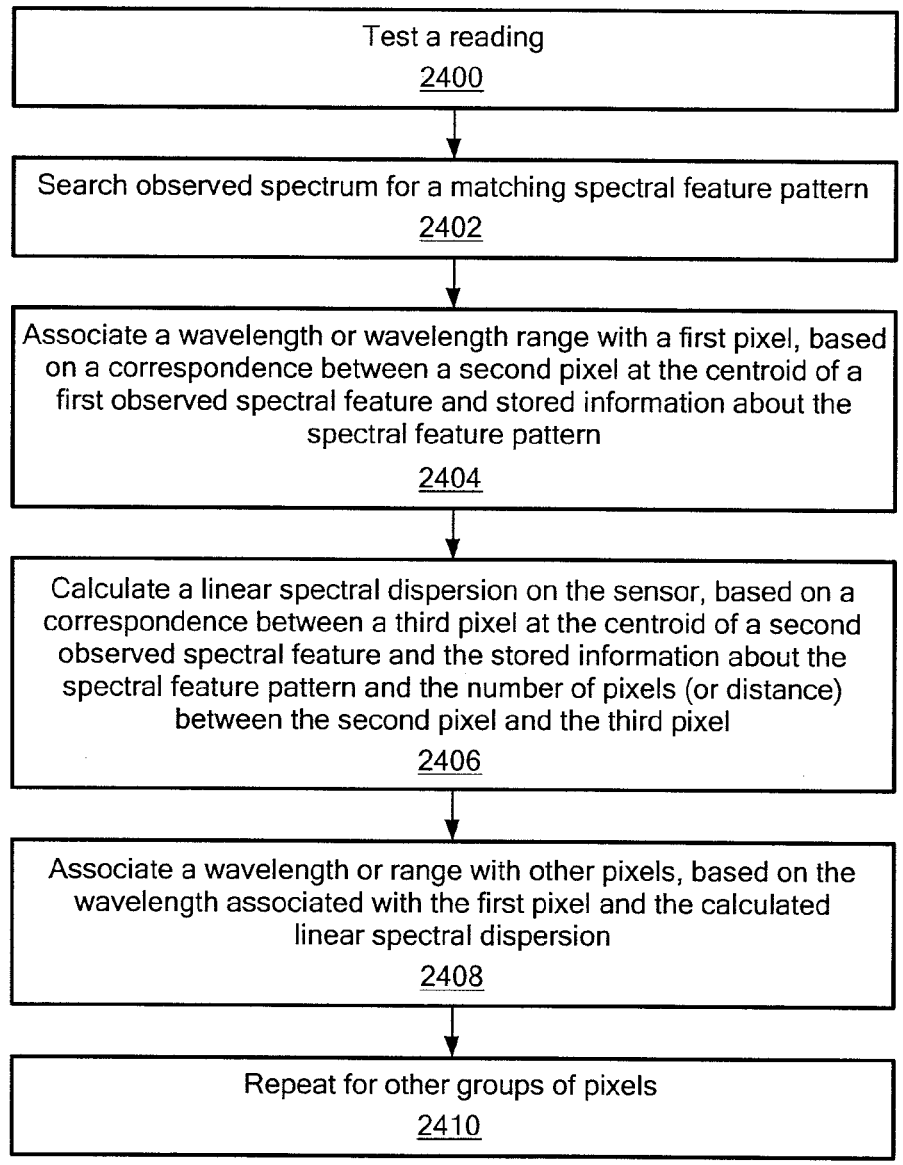
FIG. 24 is a flowchart that describes automatic wavelength calibration, according to embodiments of the present invention.

FIG. 24 is a flowchart that describes automatic wavelength calibration. At 2400, a reading is taken, i.e., a spectrum from a sample impinges on the sensors, and the processor reads at least some of the sensors. At 2402, a search is conducted of the observed spectrum and stored spectral feature patterns for a pattern that matches at least a portion of the observed spectrum. At 2404, a wavelength or range of wavelengths (hereinafter collectively referred to in this context as a wavelength) is associated with a pixel (such as the first pixel in the sensor array), based on a correspondence between a second pixel that is located at the centroid of a first observed spectral feature (such as a feature in the matched prototype) and information (such as wavelength) about the spectral feature pattern. This information may be stored in a memory.

In one embodiment, other wavelengths are assigned to other pixels based on an expected linear spectral dispersion based on the geometry of the spectrometer.

In another embodiment, at 2406, a linear spectral dispersion on the sensor is calculated, based on a correspondence between another pixel at the centroid of a second observed spectral feature and information (such as wavelength) about the second spectral feature and the number of pixels (or distance) between the two pixels at the centroids of the observed features. At 2408, a wavelength is associated with other pixels, based on the wavelength associate with the pixel at 2404 and the calculated linear spectral dispersion.

The operations at 2404 and 2406 may, collectively, associate wavelengths with all the pixels in the sensors. On the other hand, these operations may associate wavelengths with only a portion of the pixels. In that case, as indicated at 2410, necessary operations may be repeated for other groups of pixels.

Thus, the disclosed instrument may be more easily assembled or subsequently adjusted, without requiring high precision positional adjustments to the sensors. In addition, the instrument may maintain its accuracy over time and in the face of temperature-induced dimensional changes, imperfect imaging of the wandering spark source, mechanical vibration, physical shock and the like by dynamically wavelength calibrating itself, based on observed spectral features. This wavelength self-calibration may be performed automatically at the beginning of each sample run or after a predetermined number of runs, at other automatically determined times (such as between sparks or after detection of a physical shock by an accelerometer or a temperature change by a thermistor within the instrument) or in response to a user-entered command.

Diffraction Grating Mount Assembly

Figure 13:
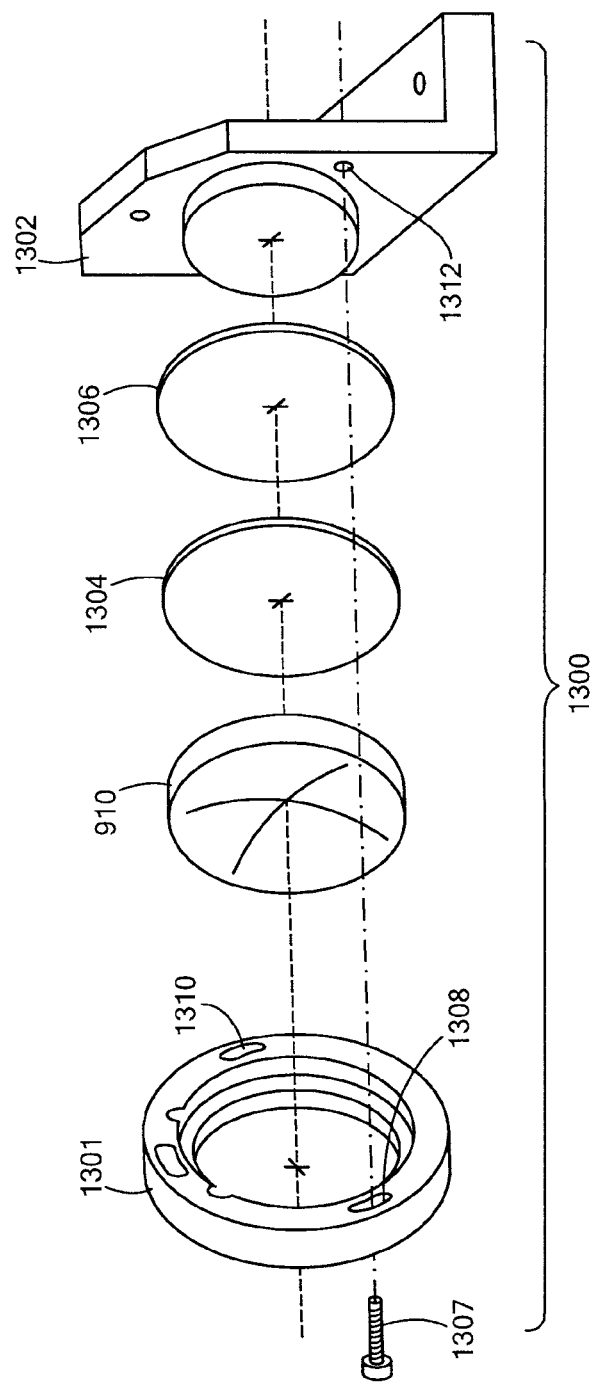
FIG. 13 is an exploded view of a diffraction grating assembly, according to one embodiment of the present invention.

FIG. 13 shows an exploded view of a diffraction grating assembly 1300. In the diffraction grating assembly 1300, the diffraction grating 910 is held between a compression ring 1301 and a diffraction grating mount 1302. Immediately behind the grating 910 is a thin (approximately 1/32-inch thick) elastomeric pad 1304, which may be cork or another suitable material. A grating compression plate 1306 is disposed between the elastomeric pad 1304 and the diffraction grating mount 1302. The compression ring 1301, the compression plate 1306 and the diffraction grating mount 1302 are preferably made from the same material as the case 900 of the spectrometer 204. The compression ring 1301 is attached to the diffraction grating mount 1202 by two screws (one of which is shown at 1307), which pass through holes 1308 and 1310 in the compression ring 1301 and thread into corresponding holes (one a which is visible at 1312) in the diffraction grating mount 1302. The compression ring 1301 applies even pressure along the perimeter of the diffraction grating 910, and the elastomeric pad 1304 enables the diffraction grating 910 to expand or contract with temperature changes without distorting the diffraction grating 910.

Figure 14:
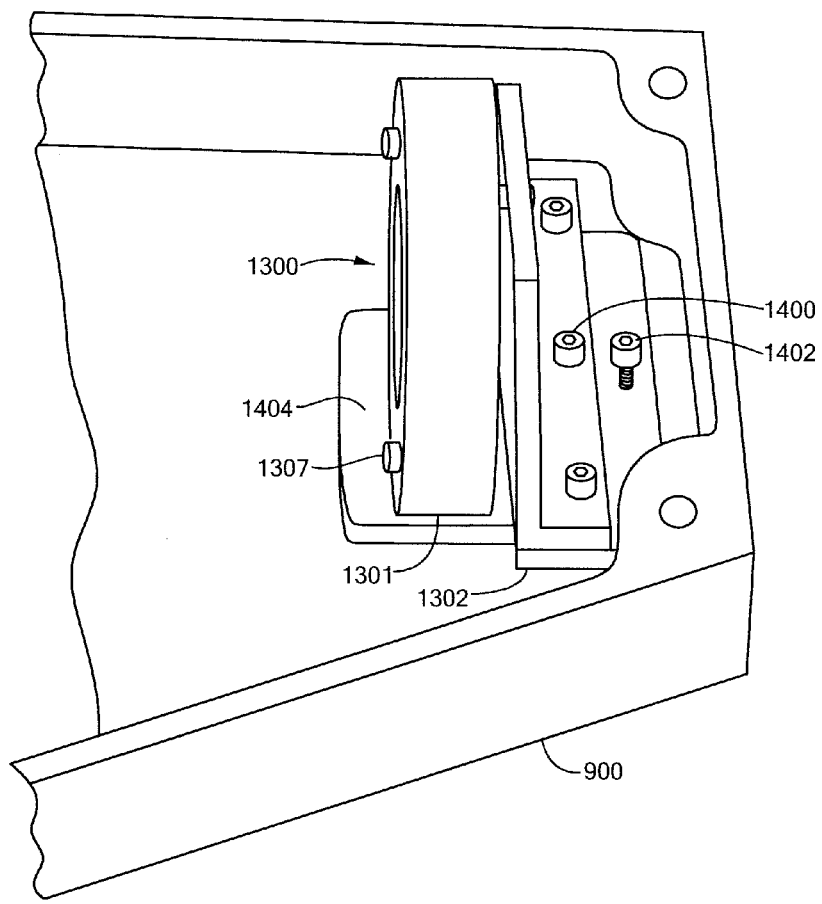
FIG. 14 is a perspective view of the diffraction grating assembly of FIG. 13 mounted within a spectrometer housing, according to one embodiment of the present invention.

The diffraction grating assembly 1300 is mounted in the diffraction grating housing 900, as shown in FIG. 14. Adjustment screws 1400 and 1402 may be used to tilt the diffraction grating assembly 1300. A well 1404 in the floor of the housing 900 provides clearance for the bottom portion of the compression ring 1301. Preferably, the diffraction grating 910 is tilted about 4° back from normal to the floor of the housing 900. Light from the prism 902 impinges on the diffraction grating 910 at an upward angle. Tilting back the diffraction grating 910 causes the dispersed light to follow a path to the sensors 912 that is approximately parallel to the floor of the housing 900.

Test Instrument Alignment

Figure 15:
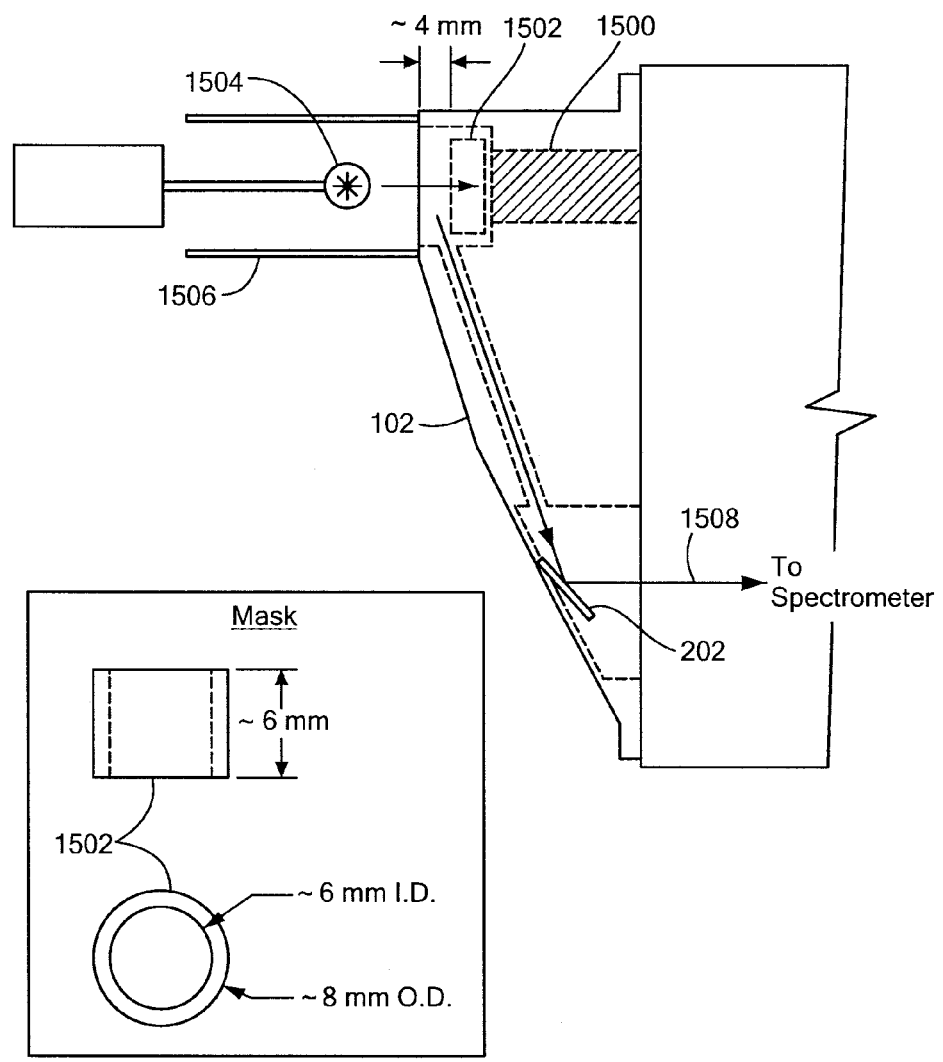
FIG. 15 is a schematic diagram of an alignment setup for the test instrument of FIG. 1, according to one embodiment of the present invention.

It may be necessary to align the optics of the test instrument 100. The mirror 202 may be aligned using a setup illustrated in FIG. 15. The counter electrode 104 is removed from the test instrument 100 and a filler block 1500 may be inserted from the back of the snout 102 to temporarily replace the counter electrode assembly. A tubular mask 1502, as illustrated by front and top news in the insert in FIG. 15, is inserted into the opening in the front of the snout 102. An ultraviolet (UV) light source 1504 is inserted into the opening in the front of the snout 102 and into the mask 1502, leading approximately 4 mm of the UV light source 1504 exposed within the opening in the front of the snout 102. The tubular mask 1502 is sized to accommodate the outside diameter of the UV light source 1504 and the inside diameter of the opening in the front of the snout 102. Additional shielding 1506 may be used to minimize UV leakage. The mirror 202 is then adjusted to maximize the amplitude of the signal 1508 reaching the spectrometer 204 (not shown).

Alternatively or in addition, a visible or invisible laser beam may be introduced into the spectrometer 204 in the vicinity of the sensors 912 and projected backwards through the spectrometer 204 to the spark gap. A port (not shown) may be provided in the housing 900 of the spectrometer 204 to facilitate introducing the laser beam. Optical components in the spectrometer 204 and the mirror 202 may be adjusted until the laser beam is detected in the opening in the front of the snout 102 where analyte emissions are expected to be produced. An expected path of the laser beam through the spectrometer may be calculated, based on the wavelength of the laser beam. It should be noted that the path taken by the laser beam toward the diffraction grating 910 may not coincide with the paths taken by some wavelengths of the optical signal dispersed by the diffraction grating 910 towards the detectors 912, due to the wavelength of the laser beam and the angle at which the diffraction grating 910 reflects light at that wavelength. Thus, sensors 912 may be clear of the port by which the laser beam is introduced into the spectrometer 204.

Further alignment may be performed by reflecting the laser beam at the opening in the front of the snout 102, back along the optical path, to the spectrometer. Alternatively or in addition, a laser beam may be introduced into the opening in the front of the snout 102 and directed along the optical path to the spectrometer.

Figure 16:
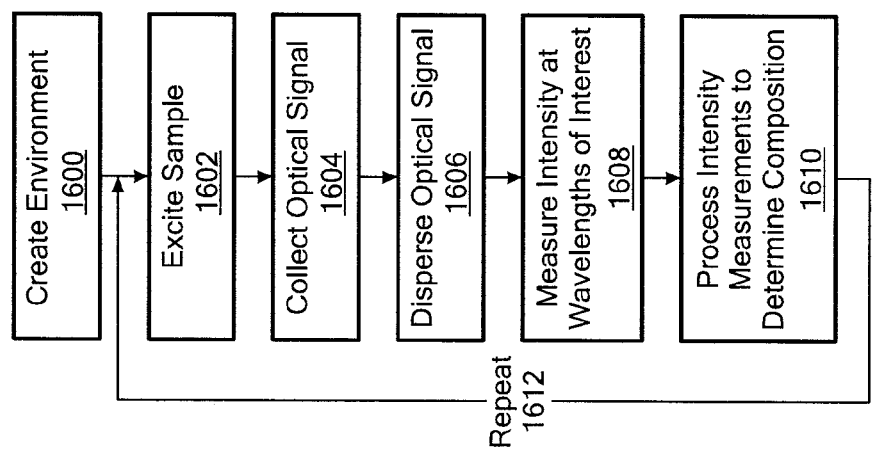
FIG. 16 is a flow chart describing a process for analyzing composition of a sample, according to one embodiment of the present invention.

FIG. 16 is a flow chart that describes a process for analyzing composition of a sample. At 1600, an environment in which a portion of the sample may be analyzed is created. Creating this environment may include purging air from the portion of the sample that is to be analyzed. An inert gas, such as argon, may be used to purge the air.

At 1602, a portion of the sample is excited. The sample may be excited with an electric spark/arc, a laser, glow discharge or another suitable mechanism. If an electric spark/arc is used, a spark gap is created between a counterelectrode and the sample. The counterelectrode and the sample are electrically connected to a spark source, which produces a suitable potential having an appropriate waveform. A potential difference between the counterelectrode and the sample breaks down the gas in an analytical gap and erodes a portion of the sample into the analytical gap. The potential may be reduced, and current may be increased, to ionize the sample material in the analytical gap. The ionize sample material emits an optical signal.

At 1604, the optical signal is collected. The optical signal is routed, via an optical path, to a spectrometer. At 1606, the optical signal is wavelength-dispersed. The optical signal may be cross-dispersed. At 1608, the intensity of the dispersed optical signal is measured at wavelengths of interest. One or more arrays of sensors may be used to measure the intensities of the dispersed optical signal. If the optical signal is cross-dispersed, one set of the sensors may be disposed a distance away from the other of the sets of sensors, according to the amount of cross-dispersion. At 1610, the intensity measurements are processed to determine the composition of the sample. The processing may be performed by a processor executing instructions stored in a memory. The process may be repeated, as indicated 1612, for a series of measurements. Data from the series of measurements may be averaged and/or parameters of the excitation (1602) may be varied for each of the repetitions.

Figure 17:
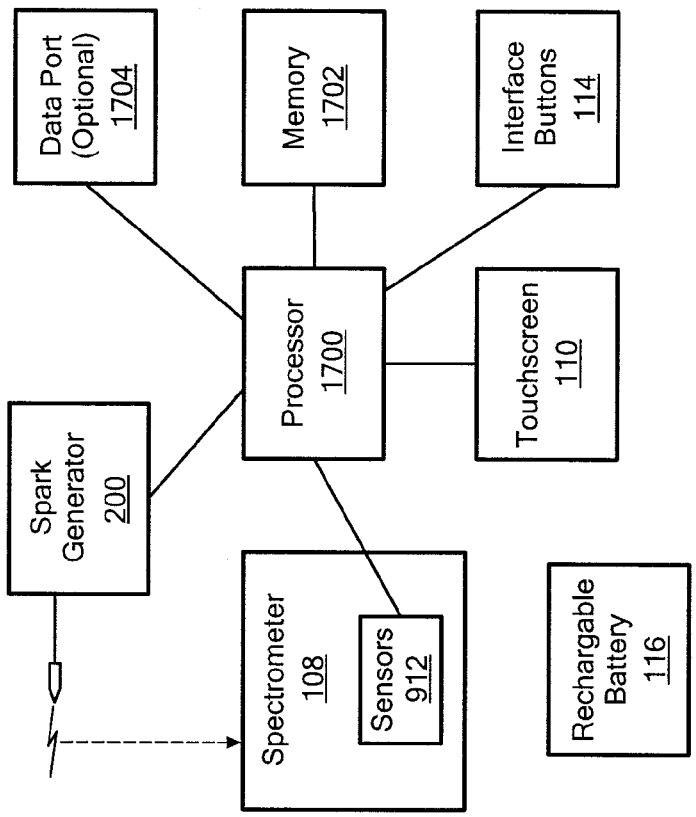
FIG. 17 is a block diagram of major components of the test instrument of FIG. 1, according to one embodiment of the present invention.

FIG. 17 is a block diagram of major components of the test instrument 100. Instructions for a processor 1700, as well as spectral feature prototypes, may be stored in a memory 1702. Analytical results from samples may also be stored in the memory 1702 and displayed on the touchscreen 110 and/or provided to an external device via a wired or wireless data port 1704. In addition, the memory 1702 may store tables of compositions of known materials (such as alloys) for comparison to compositions of test samples, and results of this comparison may be displayed on the screen 110 and/or provided via the port 1704.

Figure 18:
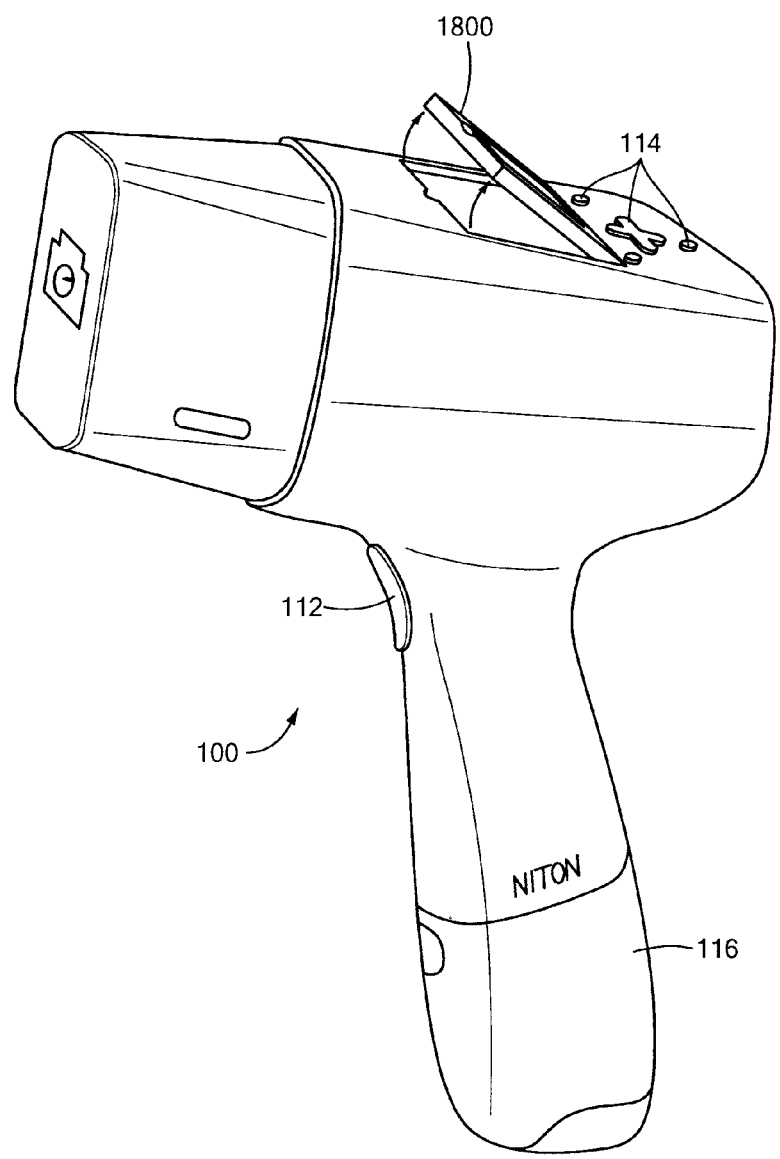
FIG. 18 is a perspective view of a hand-held, self-contained test instrument with a tilt-up screen, according to one embodiment of the present invention.

Referring to FIG. 1, the touchscreen 110 is readable while the test instrument 100 is in most orientations. However, in some cases, the touchscreen may be difficult to read. A hinged (tilt-up) screen may be used in some OES, x-ray fluorescence (XRF) or other of hand-held, self-contained test instruments. One embodiment of such a tilt-up screen is shown at 1800 in FIG. 18. A flexible ribbon cable or other suitable flexible wire is used to connect the screen 1800 to the processor or other circuitry within the test instrument 100.

Although a spectrometer having a wavelength range of about 170 nm to about 410 nm has been described, spectrometers according to the present invention may have other wavelength ranges.

A hand-held, self-contained, battery-powered test instrument has been described as including a processor controlled by instructions stored in a memory. The memory may be random access memory (RAM), read-only memory (ROM), flash memory or any other memory, or combination thereof, suitable for storing control software or other instructions and data. Some of the functions performed by the test instrument have been described with reference to flowcharts. Those skilled in the art should readily appreciate that functions, operations, decisions, etc. of all or a portion of each block, or a combination of blocks, of the flowcharts may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Furthermore, disclosed aspects, or portions of these aspects, may be combined in ways not listed above. For example, the spectrometer described above may be used in other contexts, such as terrestrial or extraterrestrial astronomy, including in combination or within telescopes and satellites. Accordingly, the invention should not be viewed as limited.

What is claimed is:

1. An analyzer for analyzing composition of a portion of a sample, comprising:
   a hand-held, self-contained, test instrument having a housing that includes:
      an exciter for exciting the portion of the sample, the excitation producing an optical signal from an analytical gap;
      a first dispersive element disposed within the hand-held instrument for receiving the optical signal and creating an intermediate optical signal dispersed in a first plane;
      a second dispersive element disposed within the hand-held instrument for dispersing the intermediate optical signal in a second plane so as to place a first resolved optical order on a corresponding first plurality of detector elements and a second resolved optical order on a corresponding second plurality of detector elements;
      a processor coupled to receive signals from the first and second pluralities of detector elements and programmed to process the signals;
      a battery powering the exciter and the processor; and
      a baffle defining an aperture, through which the intermediate optical signal passes, the baffle masking off the edges of a volume in the analytical gap.

2. An analyzer in accordance with claim 1, wherein at least one of the optical orders placed on the corresponding plurality of detector elements extends to wavelengths shorter than about 193 nm.

3. An analyzer in accordance with claim 1, wherein at least one of the optical orders placed on the corresponding plurality of detector elements extends to wavelengths shorter than about 178 nm.

4. An analyzer in accordance with claim 1, wherein at least one of the optical orders placed on the corresponding plurality of detector elements extends to wavelengths at least as short as about 170 nm.

5. An analyzer in accordance with claim 1, wherein each plurality of detector elements is configured so as to receive a continuous spectral range of the resolved optical order placed on the plurality of detector elements.

6. An analyzer in accordance with claim 5, wherein, collectively, the spectral range placed on the first and second pluralities of detector elements extends at least from about 178 nm to about 400 nm.

7. An analyzer in accordance with claim 1, wherein the optical signal is focused on the baffle.

8. An analyzer in accordance with claim 1, wherein the exciter comprises:
an electrode for sustaining an electrical potential with respect to the portion of the sample; and
a voltage supply for establishing the electrical potential on the electrode with respect to the portion of the sample.

9. An analyzer in accordance with claim 1, wherein the exciter comprises a laser.

10. An analyzer in accordance with claim 1, wherein the first dispersive element comprises a cross-dispersing prism.

11. An analyzer for analyzing composition of a portion of a sample, comprising:
a hand-held, self-contained, test instrument having a housing that includes:
an exciter for exciting the portion of the sample, the excitation producing an optical signal;
a first dispersive element disposed within the hand-held instrument for receiving the optical signal and creating an intermediate optical signal dispersed in a first plane;
a second dispersive element disposed within the hand-held instrument for dispersing the intermediate optical signal in a second plane so as to place a first resolved optical order on a corresponding first plurality of detector elements and a second resolved optical order on a corresponding second plurality of detector elements;
a processor coupled to receive signals from the first and second pluralities of detector elements and programmed to process the signals; and
a battery powering the exciter and the processor;
wherein the second dispersive element comprises a holographic diffraction grating blazed to provide comparable efficiencies in the first and second resolved optical orders.

12. An analyzer for analyzing composition of a portion of a sample, comprising:
a hand-held, self-contained, test instrument having a housing that includes:
an exciter for exciting the portion of the sample, the excitation producing an optical signal;
a first dispersive element disposed within the hand-held instrument for receiving the optical signal and creating an intermediate optical signal dispersed in a first plane;
a second dispersive element disposed within the hand-held instrument for dispersing the intermediate optical signal in a second plane so as to place a first resolved optical order on a corresponding first plurality of detector elements and a second resolved optical order on a corresponding second plurality of detector elements;
a processor coupled to receive signals from the first and second pluralities of detector elements and programmed to process the signals; and
a battery powering the exciter and the processor;
wherein:
the first plurality of detector elements is not co-planar with the second plurality of detector elements; and the test instrument further includes a mirror in an optical path of one of the first and second resolved optical orders, between the second dispersive element and the corresponding plurality of detector elements.

13. An analyzer in accordance with claim 1, wherein the first and second dispersive elements and the first and second pluralities of detector elements are rigidly coupled to a carbon-filled polymer structural member.

14. An analyzer in accordance with claim 1 wherein the first and second dispersive elements and the first and second pluralities of detector elements are rigidly coupled to a carbon-filled polymer structural member which comprises polyphenylene sulfide filled with graphite.

15. An analyzer in accordance with claim 13, wherein the carbon-filled polymer comprises polyphenylene sulfide filled with at least about 40% graphite.

16. An analyzer in accordance with claim 1, wherein the processor is programmed for automatic wavelength calibration, based on observed spectral features.

17. An analyzer in accordance with claim 1, wherein the second dispersive element provides a resolving power of at least about 5,000.

18. An analyzer in accordance with claim 1, wherein the second dispersive element provides a resolving power of at least about 10,000.

19. An analyzer in accordance with claim 1, further comprising a display screen coupled to the processor.

20. An analyzer in accordance with claim 1, further comprising a hinged display screen coupled to the processor.

21. An analyzer for analyzing composition of a portion of a sample, comprising:
a hand-held, self-contained, test instrument having a housing contacting the sample that includes:
an electrode for exciting the portion of the sample, the excitation producing an optical signal;
a spectrometer having a spectral range extending at least from about 178 nm to about 400 nm disposed in the analyzer to receive the optical signal and operative to disperse the optical signal and produce an output signal from the dispersed optical signal, including
a holographic diffraction grating having comparable efficiency in at least two different orders, and
sensors arranged to receive two orders of the dispersed optical signal from the grating ;
a processor coupled to the spectrometer and programmed to process the output signal; and
a battery powering the electrode, the spectrometer and the processor.

22. An analyzer in accordance with claim 21, wherein the spectrometer comprises a pixilated sensor, and wherein the spectrometer has a resolution of at least about 0.02 nm per pixel at about 190 nm.

23. An analyzer in accordance with claim 21, wherein the spectrometer is cross-dispersed.

24. An analyzer in accordance with claim 21, wherein the spectrometer comprises a structural member comprising a carbon-filled polymer, to which optical elements of the spectrometer are mounted.

25. An analyzer in accordance with claim 21, wherein the processor is programmed to automatically wavelength calibrate the spectrometer, based on observed spectral features.

26. An analyzer in accordance with claim 12 wherein the resolved optical order primarily composed of wavelengths that are less efficiently reflected by the mirror, impinges directly on the corresponding plurality of detector elements.

27. An analyzer in accordance with claim 12 wherein the second plurality of detector elements is oriented in a plane that is perpendicular to the first plurality of detector elements.

28. An analyzer for analyzing composition of a portion of a sample, comprising:
- a hand-held, self-contained, test instrument having a housing that includes:
    - an exciter for exciting the portion of the sample, the excitation producing an optical signal;
    - a first dispersive element disposed within the hand-held instrument for receiving the optical signal and creating an intermediate optical signal dispersed in a first plane;
    - a second dispersive element disposed within the hand-held instrument for dispersing the intermediate optical signal in a second plane so as to place a first resolved optical order on a corresponding first plurality of detector elements and a second resolved optical order on a corresponding second plurality of detector elements;
    - a processor coupled to receive signals from the first and second pluralities of detector elements and programmed to process the signals; and
    - a battery powering the exciter and the processor;
- wherein the second dispersive element comprises a diffraction grating blazed to provide comparable efficiencies in the first and second resolved optical orders.

29. An analyzer in accordance with claim 28, wherein the second dispersive element provides a resolving power of at least about 5,000.

30. An analyzer in accordance with claim 21, wherein the processor is programmed to automatically wavelength calibrate the spectrometer, based on observed spectral features.

* * * * *